US010047048B2

(12) United States Patent
Chollet

(10) Patent No.: US 10,047,048 B2
(45) Date of Patent: Aug. 14, 2018

(54) PYRROLIDINE DERIVATIVES AS OXYTOCIN/VASOPRESSIN V1A RECEPTORS ANTAGONISTS

(71) Applicant: ObsEva S.A., Plan-les-Ouates (CH)

(72) Inventor: Andre Chollet, Plan-les-Ouates (CH)

(73) Assignee: ObsEva S.A., Plan-les-Ouates (CH)

( * ) Notice: Subject to any disclaimer, the term of this patent is extended or adjusted under 35 U.S.C. 154(b) by 0 days.

(21) Appl. No.: 15/476,325

(22) Filed: Mar. 31, 2017

(65) Prior Publication Data

US 2017/0240508 A1 Aug. 24, 2017

Related U.S. Application Data

(63) Continuation of application No. 14/479,664, filed on Sep. 8, 2014, now Pat. No. 9,670,155.

(30) Foreign Application Priority Data

Sep. 10, 2013 (EP) .................................... 13183723

(51) Int. Cl.
C07D 207/09 (2006.01)
C07D 207/22 (2006.01)
A61K 9/00 (2006.01)
A61K 31/40 (2006.01)

(52) U.S. Cl.
CPC .......... *C07D 207/22* (2013.01); *A61K 9/0019* (2013.01); *A61K 9/0053* (2013.01); *A61K 31/40* (2013.01); *C07D 207/09* (2013.01)

(58) Field of Classification Search
CPC .................................................. C07D 207/09
See application file for complete search history.

(56) References Cited

U.S. PATENT DOCUMENTS

| | | | |
|---|---|---|---|
| 5,047,247 A | 9/1991 | Milovac et al. | |
| 5,069,910 A | 12/1991 | Kovacic et al. | |
| 6,329,418 B1 | 12/2001 | Cheng et al. | |
| 7,115,639 B2 | 10/2006 | Schwarz et al. | |
| 7,115,754 B2 | 10/2006 | Jorand-Lebrun et al. | |
| 7,189,754 B2 | 3/2007 | Schwarz et al. | |
| 7,211,601 B2 | 5/2007 | Halazy et al. | |
| 9,670,155 B2 | 6/2017 | Chollet | |
| 2003/0105030 A1 | 6/2003 | Liao et al. | |
| 2004/0147511 A1 | 7/2004 | Schwarz et al. | |
| 2004/0220238 A1 | 11/2004 | Schwarz et al. | |
| 2006/0004020 A1 | 1/2006 | Jorand-Lebrun et al. | |
| 2007/0037806 A1 | 2/2007 | Schwarz et al. | |
| 2007/0129381 A1 | 6/2007 | Schwarz et al. | |
| 2007/0197794 A1 | 8/2007 | Nadler et al. | |
| 2008/0038342 A1 | 2/2008 | Bergman et al. | |
| 2015/0073032 A1 | 3/2015 | Chollet | |
| 2015/0164859 A1 | 6/2015 | Chollet et al. | |
| 2016/0221944 A1 | 8/2016 | Chollet | |
| 2017/0065556 A1 | 3/2017 | Chollet et al. | |

FOREIGN PATENT DOCUMENTS

| | | |
|---|---|---|
| CN | 1678576 A | 10/2005 |
| EP | 2845850 A1 | 3/2015 |
| EP | 2886107 A1 | 6/2015 |
| JP | 2004-534804 A | 11/2004 |
| JP | 2005-533828 A | 11/2005 |
| WO | WO-1999/52868 A1 | 10/1999 |
| WO | WO-2002/074741 A1 | 9/2002 |
| WO | WO-2002/102799 A2 | 12/2002 |
| WO | WO-2004/005249 A1 | 1/2004 |
| WO | WO-2004/076407 A2 | 9/2004 |
| WO | WO-2005/082848 A2 | 9/2005 |

OTHER PUBLICATIONS

"Guidance for Industry. Drug Metabolism/Drug Interaction Studies in the Drug Development Process: Studies In Vitro," Department of Health and Human Services, U.S. Food and Drug Administration, Center for Drug Evaluation and Research, Center for Biologics Evaluation and Research, Apr. 1997 (13 pages).
Office Action for Israeli Patent Application No. 244152, dated May 23, 2016 (3 pages).
International Search Report issued in corresponding International Application No. PCT/EP2014/066075, dated Aug. 20, 2014 (3 pages).
Autism [online] retrieved from the internet on Jul. 13, 2015 (<URL:http://www.ninds.nih.gov/disorders/autism/detail_autism.htm>).
IsHak, Waguih William, et al., "Male Anorgasmia Treated with Oxytocin," J. Sex Med., pp. 1022-1024 (2008).
Office Action for Canadian Patent Application No. 2,921,580, dated May 25, 2016 (4 pages).
First Office Action for Chinese Patent Application No. 2014800499272, dated Sep. 26, 2016 (8 pages).
Notice of Reasons for Rejection for Japanese Patent Application No. 2016-535134, dated Aug. 2, 2016 (7 pages).
Pierzynski, Piotr, Oxytocin and Vasopressin V1A Receptors as New Therapeutic Targets in Assisted Reproduction, vol. 22, pp. 9-16 (2011).
Written Opinion for Singaporean Application No. 11201601743R, dated Oct. 10, 2016 (5 pages).
Farina-Lipari, E., et al., "Presence of Atrial Natriuretic Factor in Normal and Hyperplastic Human Prostate and its relationship with Oxytocin Localisation," European Journal of Histochemistry, vol. 47, Issue 2, pp. 133-138, (2003).
Assinder, S.J., et al., "Effects of Steroids on Oxytocin Secretion by the Human Prostate in vitro," International Journal of Andrology, No. 27, pp. 12-18 (2004).
Visnova, H., et al. Effects of Barusiban, A Selective Oxytocin Antagonist, on Uterine Contractility in the Luteal Phase After Controlled Ovarian Stimulation, pp. 242 (2012).
Office Action for Eurasian Patent Application No. 201690480/28, dated Jan. 31, 2017 (9 pages).

(Continued)

*Primary Examiner* — Shawquia Jackson
(74) *Attorney, Agent, or Firm* — Clark & Elbing LLP

(57) ABSTRACT

The present invention relates to a compound of formula (3Z,5S)-5-(hydroxymethyl)-1-[(2'-methyl-1,1'-biphenyl-4-yl)carbonyl]pyrrolidin-3-one O-meth19243yloxime, and/or an active metabolite thereof having antagonist action at the oxytocin receptor and/or vasopressin V1a receptor, to processes for their preparation, pharmaceutical compositions containing them and their use.

26 Claims, 3 Drawing Sheets

(56) References Cited

OTHER PUBLICATIONS

International Preliminary Report on Patentability for International Application No. PCT/EP2014/066075, dated Sep. 7, 2015 (5 pages).
Shinghal, Rajesh MD., et al., "Safety and Efficacy of Epelsiban in the Treatment of Men with Premature Ejaculation: A Randomized, Double-Blind, Placebo-Controlled, Fixed-Dose Study," J Sex Med, pp. 1-12 (2013).
Moraloglu, Ozlem, et al., "Treatment with Oxytocin Antagonists before Embryo Transfer May Increase Implantation Rates after IVF," vol. 21, pp. 338-343 (2010).
Assinder, S.J., "Oxytocin Increases 5alpha-Reductase Activity of Human Prostate Epithelial Cells, But Not Stromal Cells," The Prostate 68, pp. 115-121 (2008).
Decision of Rejection for Japanese Patent Application No. 2016-535134, dated Dec. 6, 2016 (10 pages).
Nicholson, Helen D., "Oxytocin: A Paracrine Regulator of Prostatic Function," Reviews of Reproduction 1, pp. 69-72, (1996).
Fanchin, Renato, et al., "Uterine Contractions at the Time of Embryo Transfer After Pregnancy Rates after In-Vitro Fertilization," vol. 13, No. 7, pp. 1968-1974 (1998).
Office Action for Korean Patent Application No. 10-2016-7009235, dated Aug. 23, 2016 (9 pages).
Murphy, Michael R., et al., "Changes in Oxytocin and Vasopressin Secretion During Sexual Activity in Men," Journal of Clinical Endocrinology and Metabolism, vol. 65, No. 4, pp. 738-741 (1987).
Clement, P., et al., "Brain Oxytocin Receptors Mediate Ejaculation Elicited by 7-hydroxy-2-(di-N-propylamino) tetralin (7-OH-DPAT) in Anaesthetized Rats," British Journal of Pharmacology, pp. 1150-1159 (2008).
Blockeel, C., et al., "Effects of Barusiban and Atosiban on Frequency of Uterine Contractions in the Luteal Phase after Stimulation: A Randomised Placebo-Controlled Trial," (2009).
Written Opinion for International Patent Application No. PCT/EP2014/066075, dated Aug. 20, 2014 (4 pages).
Saniger, Marcela Arrazola, et al., "Alpha-1-Adrenergic Receptor Blockade Modifies Insulin-Regulated Aminopeptidase (IRAP) Activity in Rat Prostate and Modulates Oxytocin Functions," Drug Metabolism Letters, vol. 5, No. 3, pp. 1-5 (2011).
Basic Operation I, New Experimental Chemistry Lecture 1, Incorporated Chemical Society of Japan Part, Jun. 10, 1985, Ver. 6, p. 341 to p. 351.
Basis of Experiment/Information, Basic Part I, Experimental Chemistry Lecture 1, Incorporated Chemical Society of Japan Part, Ver. 5, Sep. 25, 2003, p. 208 to p. 211.
Guideline for Trials, Bioequivalence to Generic Drugs, Feb. 29, 2012, Pharmaceutical Safety and Environmental Health bureau, Ministry of Health, Labor and Welfare, PFXB/ELD Notification No. 0229.10, Appendix 1.
Organic Polymer Biochemistry, Basic Part IV, Experimental Chemistry Lecture 4, Incorporated Chemical Society of Japan Part, Ver. 5, Sep. 25, 2003, p. 95 to p. 108.
Q & A, Guideline for Trials, Bioequivalence to Generic Drugs, Feb. 29, 2012, Pharmaceutical Safety and Environmental Health bureau, Ministry of Health, Labor and Welfare, Office Notification Appendix 1.
Notice of Reasons for Rejection for Japanese Patent Application No. 2016-535134, dated May 30, 2017 (71 pages).
Vrachnis et al. The Oxytocin-Oxytocin Receptor System and its Antagonists as Tocolytic Agents. International Journal of Endocrinology, Jan. 8, 2011.
Mazzanti et al., "Rotation in Biphenyls with a Single Ortho-Substituent", J. Org. Chem. 71:5474-81 (2006).
Lynch et. al., "The Effect of Cytochrome P450 Metabolism on Drug Response, Interactions, and Adverse Effects," Am Fam Physician. 76:391-396 (2007).
Notification of Reasons for Refusal for Japanese Patent Application No. 2017-076326, dated Feb. 28, 2018 (6 pages).

Schematic TLC profile of the collected fractions

PYRROLIDINE DERIVATIVES AS OXYTOCIN/VASOPRESSIN V1A RECEPTORS ANTAGONISTS

CROSS REFERENCE TO RELATED APPLICATIONS

This application is a continuation of, and claims priority to, U.S. patent application Ser. No. 14/479,664, now U.S. Pat. No. 9,670,155, filed Sep. 8, 2014, which claims priority to European Patent Application No. 13183723.9, filed Sep. 10, 2013, the contents of which are incorporated herein by reference in their entirety.

TECHNICAL FIELD

The present invention relates to a compound of formula (3Z,5S)-5-(hydroxymethyl)-1-[(2'-methyl-1,1'-biphenyl-4-yl)carbonyl]pyrrolidin-3-one O-methyloxime, and/or an active metabolite thereof having antagonist action at the oxytocin receptor and/or vasopressin V1a receptor, to processes for their preparation, pharmaceutical compositions containing them and their use in medicine.

BACKGROUND OF THE INVENTION

Oxytocin (OT) is a cyclic nona-peptide that mediates its physiological actions through activation of the oxytocin receptor (OT-R), a cell membrane receptor belonging to the class of G protein-coupled receptors that is similar to arginine vasopressin receptors. One important action of Oxytocin (OT) is to cause the contraction of the uterus of mammals during labor. Repeated, concerted and regular contraction of the uterus will cause the dilatation of the cervix, the rupture of fetal membranes and lead to expulsion of the fetus. Premature labor is when these contractions occur before the normal term of pregnancy. Preterm increase of uterine activity is the most common expression of preterm labor.

Premature labor leads to undesired premature birth, a serious health problem that remains the major cause of perinatal mortality and severe morbidity, especially respiratory distress syndrome, intraventricular haemorrhage, bronchopulmonary dysplasia and necrotising enterocolitis that are far more common in preterm than in term infants. Long-term impairments such as cerebral palsy, visual impairment and hearing loss are also more common in preterm infants. Nowadays, preterm birth remains the leading cause of infant mortality and morbidity in industrialized nations, where, despite the significant improvements in obstetrical medicine, it is causing high costs for neonatal intensive care of premature babies. The actual costs are even higher to society when taking into consideration the healthcare provision of preterm childbirth-related ailments, such as respiratory distress syndrome, heart conditions, cerebral palsy, epilepsy, and severe learning disabilities. The management of preterm labor represents a significant problem in the field of obstetrics.

The OT/OT-R system plays a vital role in initiating labor in mammals, in particular in humans. The density of OT-R increases markedly in the myometrium before the onset and during labor. Also it is thought that the local OT peptide hormone concentration increases markedly before parturition in human. The high circulating concentrations of progesterone induce uterine quiescence while the uterus acquires contractile ability. Shortly before term, plasma progesterone concentrations fall, OT-R expression in the uterus increases markedly, OT is released and uterine contractile activity increases. At term, the contractions rise to a crescendo, resulting in delivery as a result of two interacting positive feedback loops. The first is a local uterine loop: within the uterus itself, contractile prostaglandins are produced and released in response to OT and uterine contractions. These prostaglandins may play a further role in cervical ripening and weakening of fetal membranes. The second loop involves the hypothalamus: in response to uterine contractions and vaginal and cervical distension, magnocellular oxytocin neurons in the hypothalamus increase their activity resulting in the release of OT from their axon terminals in the posterior pituitary. The released OT acts upon the uterus both to stimulate the further production of prostaglandins and to contribute further to the contractions of the uterus.

Therefore, blocking the effect of OT by antagonizing OT-R might represent an attractive modality for the treatment of diseases related to the OT-R activity, in particular preterm labor.

Tocolytic, i.e. uterus relaxing agents, have been used in clinical studies for the pharmaceutical treatment of preterm labor. Most of these agents are used off-label. They have shown very limited efficacy, if any, in prolonging gestation and without clear demonstration of improvement of neonate outcome. Current tocolytics are very often associated with unwanted adverse effects on women, foetus or neonate. Such tocolytics include beta-2-adrenergic agonists, prostaglandin synthesis inhibitors, magnesium sulfate, nitric acid donors and calcium channel blockers. Beta-2-adrenergic agonists such as ritodrine or terbutaline cause a number of cardiovascular and metabolic side effects including maternal tachycardia, palpitations, hypotension, altered thyroid function and fetal and neonatal hypoglycaemia, tachycardia. Ritodrine is no longer FDA approved. The calcium channel blocker nifedipine is also a medicine that is used to try to stop contractions. Some of the side effects that may occur include facial flushing, headache, nausea, palpitations, and lighthcadedness. The total prostaglandin synthesis inhibitor (NSAID) indomethacin has been used. It can also have serious effects on the fetus: constriction of ductus arteriosus, pulmonary hypertension, decrease in renal function with oligohydramnios, intraventricular hemorrhage, hyperbilirubinemia, necrotizing enterocolitis. Maternal side effects include abdominal discomfort, nausea, vomiting, depression and dizzy spells for the mother. Another NSAID is sulindac that has a side effect profile similar to indomethacin. For magnesium sulfate, meta-analyses have failed to support it as a tocolytic agent. Women reported important side effects such as flushing, lethargy, headache, muscle weakness, pulmonary edema and cardiac arrest. A newborn who has been exposed to magnesium sulfate may show lethargy, hypotonia, respiratory depression, bone problems, osteopenia and fractures. Recently, the FDA is advising healthcare professionals against using magnesium sulfate injection for longer than 5-7 days to stop preterm labor in women.

Atosiban, a dual vasopressin V1a receptor and OT-R antagonist is marketed in EU and used to stop contractions and delay preterm delivery by a few days. Atosiban is a peptide that is not orally bioavailable and must be administered parenterally. It is rapidly degraded in circulation by enzymes and its use is limited to maximum 48 h.

In addition, non-peptide OT-R antagonists were developed such as pyrrolidine derivatives (WO 01/72705, WO 02/102799, WO 2002/074741, WO 2004/005249) as mixtures of isomers.

There remain significant unmet needs for efficient and orally selective OT-R antagonist for the treatment of diseases related to the OT-R activity, in particular preterm labor.

SUMMARY OF THE INVENTION

The present invention provides a compound of formula (3Z,5S)-5-(hydroxymethyl)-1-[(2'-methyl-1,1'-biphenyl-4-yl)carbonyl]pyrrolidin-3-one O-methyloxime, and/or an active metabolite thereof.

The invention also provides a compound of formula (3Z,5S)-5-(hydroxymethyl)-1-[(2'-methyl-1,1'-biphenyl-4-yl)carbonyl]pyrrolidin-3-one O-methyloxime, and/or an active metabolite thereof, for use as a medicament and pharmaceutical compositions comprising said compound.

Also provided is a compound of formula (3Z,5S)-5-(hydroxymethyl)-1-[(2'-methyl-1,1'-biphenyl-4-yl)carbonyl]pyrrolidin-3-one O-methyloxime, and/or an active metabolite, for the treatment and/or prevention of disorders associated with the oxytocin receptor activity and/or vasopressin V1a receptor activity.

The invention further provides a process for preparing and isolating a compound of formula (3Z,5S)-5-(hydroxymethyl)-1-[(2'-methyl-1,1'-biphenyl-4-yl)carbonyl]pyrrolidin-3-one O-methyloxime, and/or an active metabolite thereof in substantially pure form.

Figure 1A:
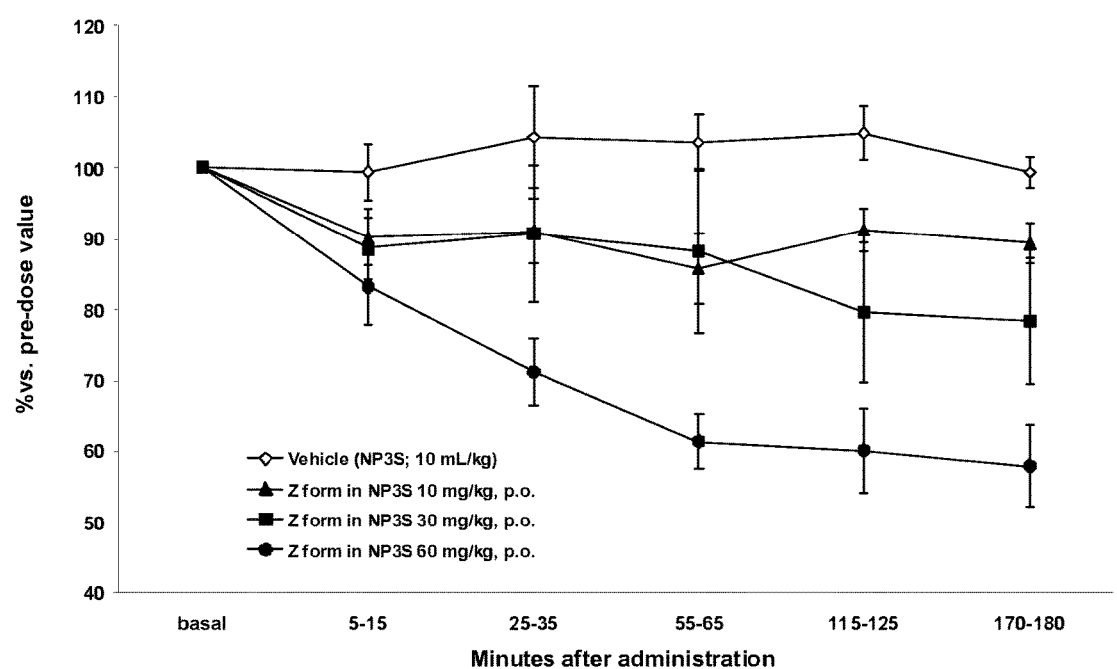
FIGS. 1A and 1B describe dose-response effects of the Z-isomer and E-isomer administered by oral route on inhibition of spontaneous uterine contractions in anesthetized pregnant rats near term (gestational days 19-21). Data as means±S.E. of n=6-8 animals per group. The y-axis represents uterine contractions as % of value compared to pre-dose set at 100%. The x-axis represents the time post-dose in minutes. Contractions were continuously recorded and area-under-the-curve (AUC) integrated over 10-min time intervals.

The results presented in FIG. 1A demonstrate that (3Z, 5S)-5-(hydroxymethyl)-1-[(2'-methyl-1,1'-biphenyl-4-yl)carbonyl]pyrrolidin-3-one O-methyloxime (Z form) is capable of rapidly inhibiting spontaneous uterine contractions in anesthetized late-term pregnant rat at various doses (10, 30 or 60 mg/kg) compared to control vehicle NP3S (5% N-methylpyrrolidone, 25% polyethyleneglycol 200, 30% polyethylene glycol 400, 20% propylene glycol, 20% saline). Uterine contractions inhibition of 15% can be observed 5 to 15 min after administration of the substantially pure Z form. Efficient inhibition of 42% is observed 170-180 minutes after administration of said compound.

Figure 1B:
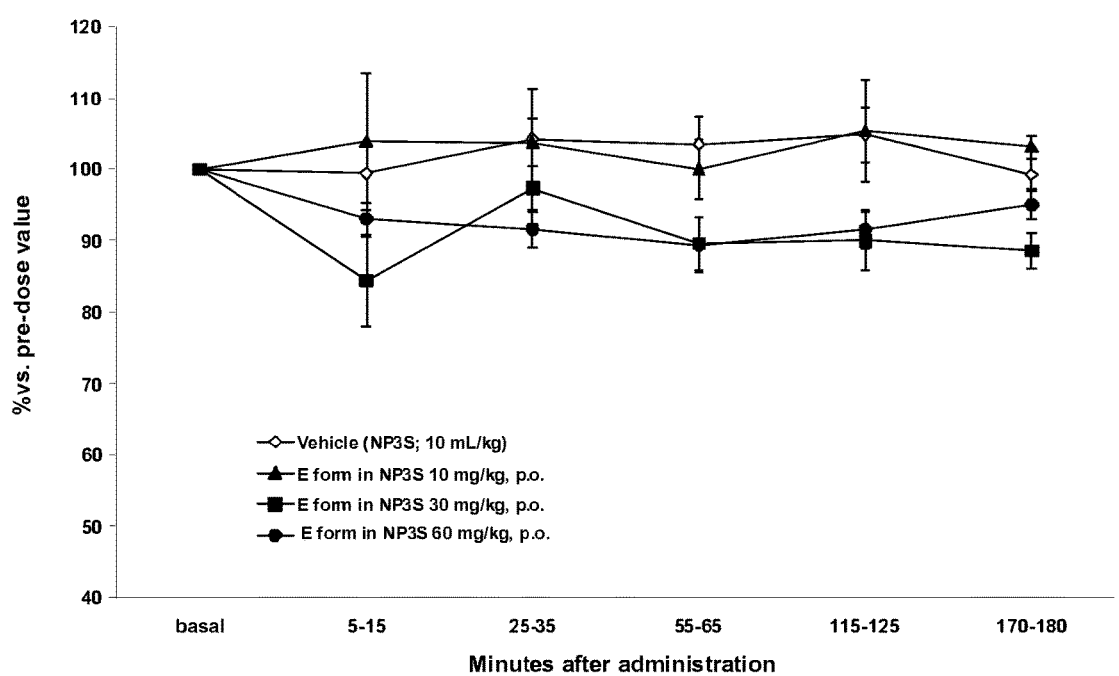

In contrast, no inhibition of uterine contraction has been observed with (3E,5S)-5-(hydroxymethyl)-1-[(2'-methyl-1,1'-biphenyl-4-yl)carbonyl]pyrrolidin-3-one O-methyloxime at various doses (10, 30 or 60 mg/kg, E form) at any time during the 170-180 minutes observation (FIG. 1B).

Figure 2:
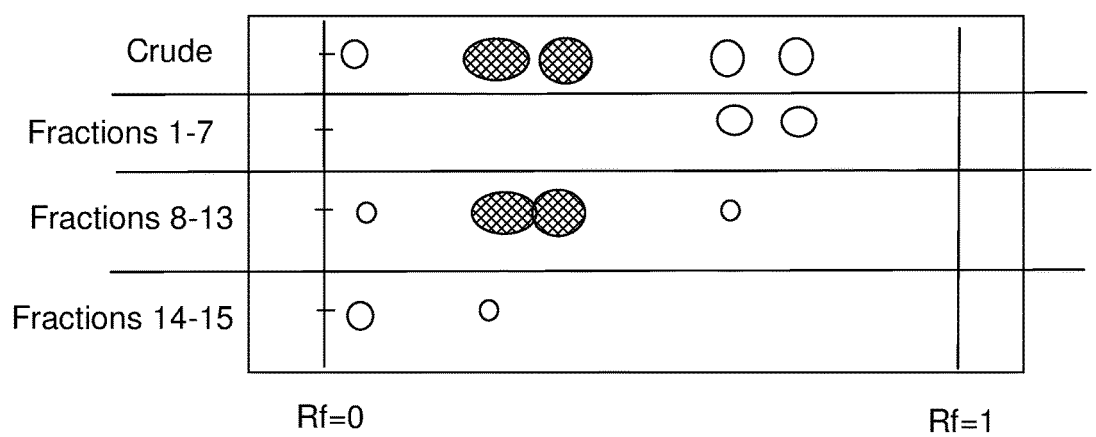

FIG. 2 is a schematic TLC profile showing the results of a dry flash chromatography purification of a crude isomeric mixture of (3Z/E,5S)-5-(hydroxymethyl)-1-[(2'-methyl-1,1'-biphenyl-4-yl)carbonyl]pyrrolidin-3-one O-methyloxime. As described in Example 1, below, a crude mixture of (3Z/E,5S)-5-(hydroxymethyl)-1-[(2'-methyl-1,1'-biphenyl-4-yl)carbonyl]pyrrolidin-3-one O-methyloxime concentrated to dryness was re-dissolved in 2 volume toluene and loaded onto a pad of SiO2 (5 wt) prior to elution using 25 volume fractions of eluent. Fractions 1-5 were eluted with pure toluene; fractions 6-10 were eluted with toluene/MeOH 1% vol/vol; and fractions 10-15 were eluted with toluene/MeOH 2% vol/vol. The Z and E forms are shown by shaded spots. Fractions 8 to 13 were combined and concentrated to dryness. The results show a recovery of 75%. There was no improvement in the E/Z ratio. A minor gain of about 4% area in purity of the isomeric mixture (E+Z) was observed before and after dry-flash chromatography.

DETAILED DESCRIPTION OF THE INVENTION

The present invention relates to the compound of formula (3Z,5S)-5-(hydroxymethyl)-1-[(2'-methyl-1,1'-biphenyl-4-yl)carbonyl]pyrrolidin-3-one O-methyloxime, and/or an active metabolite thereof, said compound being in the Z isomeric configuration at the O-methyloxime functional group.

The compound of formula (3E,5S)-5-(hydroxymethyl)-1-[(2'-methyl-1,1'-biphenyl-4-yl)carbonyl]pyrrolidin-3-one O-methyloxime differs from compounds of the present invention at the O-methyloxime functional group being in the E isomeric configuration.

As used herein, the term "active metabolite thereof" refers to a product produced through metabolism in the body or in vitro of a specified compound, in the present case (3Z,5S)-5-(hydroxymethyl)-1-[(2'-methyl-1,1'-biphenyl-4-yl)carbonyl]pyrrolidin-3-one O-methyloxime and which exhibits the same biological activity as (3Z,5S)-5-(hydroxymethyl)-1-[(2'-methyl-1,1'-biphenyl-4-yl)carbonyl]pyrrolidin-3-one O-methyloxime.

Active metabolites of (3Z,5S)-5-(hydroxymethyl)-1-[(2'-methyl-1,1'-biphenyl-4-yl)carbonyl]pyrrolidin-3-one O-methyloxime may be identified using routine techniques known in the art and their activities determined using tests such as those described herein. Such metabolites may result for example from the oxidation, glucuronidation or other conjugation, hydrolysis, reduction and the like, of the administered Z form. Accordingly, the invention includes active metabolites of (3Z,5S)-5-(hydroxymethyl)-1-[(2'-methyl-1,1'-biphenyl-4-yl)carbonyl]pyrrolidin-3-one O-methyloxime, including compounds produced by a process comprising contacting a compound of this invention with a mammal for a period of time sufficient to yield a metabolic product thereof. Such metabolite may also be produced in vitro by oxidation, reduction, hydrolysis, glucuronidation or other conjugation transformation of the corresponding (3Z,5S)-5-(hydroxymethyl)-1-[(2'-methyl-1, 1'-biphenyl-4-yl)carbonyl]pyrrolidin-3-one O-methyloxime. Examples of actives metabolites of (3Z,5S)-5-(hydroxymethyl)-1-[(2'-methyl-1,1'-biphenyl-4-yl)carbonyl]pyrrolidin-3-one O-methyloxime, include compounds those structures are shown below:

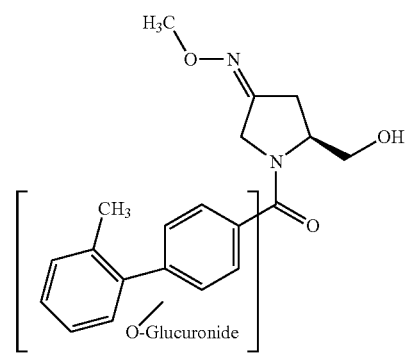

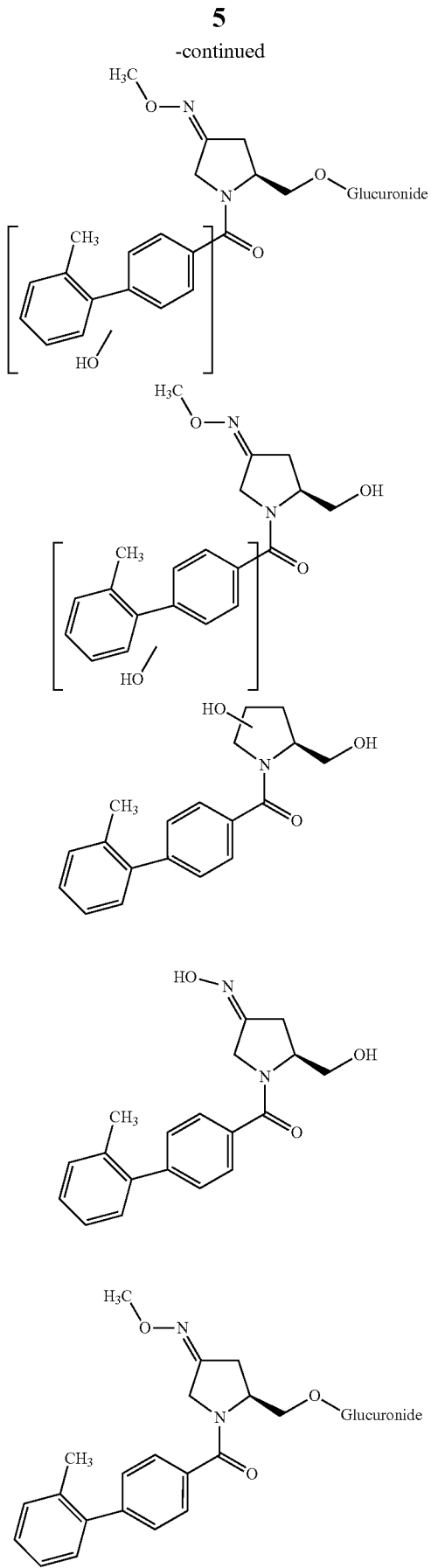

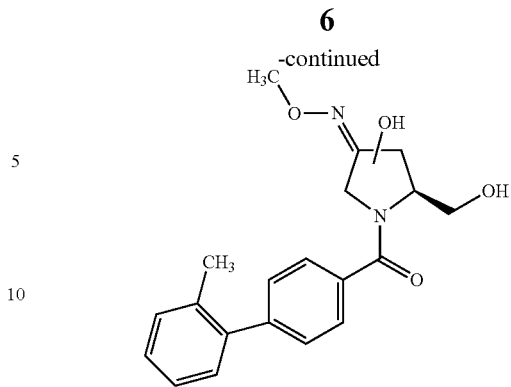

A compound which, upon administration to the recipient, is capable of being converted into a compound of (3Z,5S)-5-(hydroxymethyl)-1-[(2'-methyl-1,1'-biphenyl-4-yl)carbonyl]pyrrolidin-3-one O-methyloxime, and/or an active metabolite thereof as described above, is known as a "prodrug". A prodrug may, for example, be converted within the body, e. g. by hydrolysis in the blood, into its active form that has medical effects. Pharmaceutical acceptable prodrugs are described in T. Higuchi and V. Stella, Prodrugs as Novel Delivery Systems, Vol. 14 of the A. C. S. Symposium Series (1976); "Design of Prodrugs" ed. H. Bundgaard, Elsevier, 1985; and in Edward B. Roche, ed., Bioreversible Carriers in Drug Design, American Pharmaceutical Association and Pergamon Press, 1987, which are incorporated herein by reference.

The compound of the present invention is produced by methods such as those disclosed for example in WO2004/005249 and WO2005/082848. However, said compound is synthesized and obtained in isomeric mixtures (3Z/E,5S)-5-(hydroxymethyl)-1-[(2'-methyl-1,1'-biphenyl-4-yl)carbonyl]pyrrolidin-3-one O-methyloxime comprising (3Z,5S)-5-(hydroxymethyl)-1-[(2'-methyl-1,1'-biphenyl-4-yl)carbonyl]pyrrolidin-3-one O-methyloxime and (3E,5S)-5-(hydroxymethyl)-1-[(2'-methyl-1,1'-biphenyl-4-yl)carbonyl]pyrrolidin-3-one O-methyloxime.

Thus, the present invention relates to a compound of formula (3Z/E,5S)-5-(hydroxymethyl)-1-[(2'-methyl-1,1'-biphenyl-4-yl)carbonyl]pyrrolidin-3-one O-methyloxime, and/or an active metabolite thereof comprising at least 85% to 100% of a compound of formula (3Z,5S)-5-(hydroxymethyl)-1-[(2'-methyl-1,1'-biphenyl-4-yl)carbonyl]pyrrolidin-3-one O-methyloxime and/or metabolite thereof, preferably 85% to 99.9%, more preferably 90% to 99.9%, and even more preferably 95% to 99.9% of said compound.

Alternatively, the present invention relates to a compound of formula (3Z,5S)-5-(hydroxymethyl)-1-[(2'-methyl-1,1'-biphenyl-4-yl)carbonyl]pyrrolidin-3-one O-methyloxime, and/or an active metabolite thereof, provided in substantially pure form.

As used herein, the term "substantially pure" refers to a compound provided in a form which is substantially free of other compounds. Examples of said "other compounds" include (3E,5S)-5-(hydroxymethyl)-1-[(2'-methyl-1,1'-biphenyl-4-yl)carbonyl]pyrrolidin-3-one O-methyloxime, (3Z,5S)-5-(hydroxymethyl)-1-[(2'-methyl-1,1'-biphenyl-4-yl)carbonyl]pyrrolidin-3-one, (3Z,5S)-5-(hydroxymethyl)-1-[(2'-methyl-1,1'-biphenyl-4-yl)carbonyl]pyrrolidin-3-one oxime, (3R,5S)-5-(hydroxymethyl)-1-[(2'-methyl-1,1'-biphenyl-4-yl)carbonyl]-3-methoxyamino-pyrrolidine, (3S,5S)-5-(hydroxymethyl)-1-[(2'-methyl-1,1'-biphenyl-4-yl)carbonyl]-3-methoxyamino-pyrrolidine, (3Z,5S)-5-(O-[(2'-methyl-1,1'-biphenyl-4-yl)carbonyl]pyrrolidin-3-one O-methyloxime and (3E,5S)-5-(O-[(2'-methyl-1,1'-biphenyl-4-yl)carbonyl]pyrrolidin-3-one O-methyloxime.

Most preferably, the compound of formula (3Z,5S)-5-(hydroxymethyl)-1-[(2'-methyl-1,1'-biphenyl-4-yl)carbonyl]pyrrolidin-3-one O-methyloxime, and/or an active metabolite thereof is substantially free of the compound of formula (3E,5S)-5-(hydroxymethyl)-1-[(2'-methyl-1,1'-biphenyl-4-yl)carbonyl]pyrrolidin-3-one O-methyloxime.

Even more preferably, the purity of a substantially pure form compound of formula (3Z,5S)-5-(hydroxymethyl)-1-[(2'-methyl-1,1'-biphenyl-4-yl)carbonyl]pyrrolidin-3-one O-methyloxime, and/or an active metabolite thereof, is at least 55%, at least 60%, at least 65%, at least 70%, at least 75%, at least 80%, at least 85%, at least 90%, at least 95%, at least 98%, at least 99%, at least 99.2%, at least 99.3%, at least 99.4%, at least 99.5%, at least 99.6%, at least 99.7%, at least 99.8%, at least 99.9% or at least 100% and is therefore substantially free of compound of formula (3E,5S)-5-(hydroxymethyl)-1-[(2'-methyl-1,1'-biphenyl-4-yl)carbonyl]pyrrolidin-3-one O-methyloxime, i.e less than 45%, less than 35%, less than 25%, less than 15%, less than 10%, less than 5%, less than 3%, more preferably less than 2%, even more preferably less than 1%.

Even more preferably, the purity of the substantially pure form compound of formula (3Z,5S)-5-(hydroxymethyl)-1-[(2'-methyl-1,1'-biphenyl-4-yl)carbonyl]pyrrolidin-3-one O-methyloxime, and/or an active metabolite thereof, is at least in the range of 85% to 100%, preferably 85% to 99.9%, more preferably 90% to 99.9%, and even more preferably in the range of 95% to 99.9%.

Depending on the nomenclature used, the compound of the invention "(3Z,5S)-5-(hydroxymethyl)-1-[(2'-methyl-1,1'-biphenyl-4-yl)carbonyl]pyrrolidin-3-one O-methyloxime" can also be defined as "(4Z,2S)-2-(hydroxymethyl)-1-[(2'-methyl-1,1'-biphenyl-4-yl-carbonyl)]pyrrolidine-4-one O-methyloxime.

Generally, the compound of formula (3Z,5S)-5-(hydroxymethyl)-1-[(2'-methyl-1,1'-biphenyl-4-yl)carbonyl]pyrrolidin-3-one O-methyloxime, and/or an active metabolite thereof, is an oxytocin receptor antagonist.

As used herein, the term "oxytocin receptor antagonist" refers to a compound that functions by inhibiting (partially or completely) or blocking the oxytocin receptor (OT-R), thereby preventing activation of the receptor by oxytocin.

The present invention provides a compound of formula (3Z,5S)-5-(hydroxymethyl)-1-[(2'-methyl-1,1'-biphenyl-4-yl)carbonyl]pyrrolidin-3-one O-methyloxime and/or an active metabolite thereof wherein said compound is a partial or complete oxytocin receptor antagonist and wherein the inhibitor constant Ki is less than about 1 µM. Preferably, said inhibitor constant Ki is less than about 0.1 µM, more preferably less than about 0.06 µM.

The present invention further provides a compound of formula (3Z,5S)-5-(hydroxymethyl)-1-[(2'-methyl-1,1'-biphenyl-4-yl)carbonyl]pyrrolidin-3-one O-methyloxime and/or an active metabolite thereof wherein said compound is an oxytocin receptor antagonist and wherein the half maximal inhibitory concentration IC50 is less than about 1 µM. Preferably, said IC50 is less than about 0.1 µM, more preferably less than about 0.09 µM.

Generally also, the compound of formula (3Z,5S)-5-(hydroxymethyl)-1-[(2'-methyl-1,1'-biphenyl-4-yl)carbonyl]pyrrolidin-3-one O-methyloxime, and/or an active metabolite thereof, is a vasopressin V1a receptor antagonist.

As used herein, the term "vasopressin V1a receptor antagonist" refers to a compound that functions by inhibiting (partially or completely) or blocking the vasopressin V a receptor (also known as Arginine vasopressin receptor 1A), thereby preventing activation of the receptor by vasopressin. Vasopressin V1a receptor is one of the three major receptor types for the peptide hormone arginine vasopressine, the others being V1b and V2 receptors Preferably, the compound of formula (3Z,5S)-5-(hydroxymethyl)-1-[(2'-methyl-1,1'-biphenyl-4-yl)carbonyl]pyrrolidin-3-one O-methyloxime and/or an active metabolite thereof is a vasopressin V1a receptor antagonist, wherein the inhibitor constant Ki is less than about 1 µM. Most preferably, said inhibitor constant Ki is less than about 0.5 µM, even more preferably less than about 0.15 µM.

The present invention also relates to a compound of formula (3Z,5S)-5-(hydroxymethyl)-1-[(2'-methyl-1,1'-biphenyl-4-yl)carbonyl]pyrrolidin-3-one O-methyloxime, and/or an active metabolite thereof, that is an oxytocin receptor antagonist and a vasopressin V1a receptor antagonist.

Usually, the compound of formula (3Z,5S)-5-(hydroxymethyl)-1-[(2'-methyl-1,1'-biphenyl-4-yl)carbonyl]pyrrolidin-3-one O-methyloxime, and/or an active metabolite thereof, inhibits the uterine contractions. Advantageously, said compound inhibits uterine contractions rapidly in a time lapse of 2-30, preferably 5-20 minutes following its administration.

Surprisingly, the Applicants have shown that the inhibitory activity is specific to the substantially pure Z form of formula (3Z,5S)-5-(hydroxymethyl)-1-[(2'-methyl-1,1'-biphenyl-4-yl)carbonyl]pyrrolidin-3-one O-methyloxime, and/or metabolite thereof. As shown in the Examples, the substantially pure E form of formula (3E,5S)-5-(hydroxymethyl)-1-[(2'-methyl-1,1'-biphenyl-4-yl)carbonyl]pyrrolidin-3-one O-methyloxime shows no efficacy as it does not inhibit the uterine contractions.

The dosage regimen regarding the compound of the present invention and/or an active metabolite thereof is selected in accordance with a variety of factors including type, species, age, weight, sex and medical condition of the patient; the severity of the condition to be treated; the route of administration; the renal and hepatic function of the patient; and the particular compound or active metabolite thereof employed. An ordinarily skilled physician can readily determine and prescribe the effective amount of the drug required to prevent, counter or arrest the progress of the condition.

Advantageously, a compound of the present invention and/or an active metabolite thereof may be administered in a single dose, or the total dosage may be administered in divided doses of two, three or four times daily.

Preferably, the present invention provides a compound of formula (3Z,5S)-5-(hydroxymethyl)-1-[(2'-methyl-1,1'-biphenyl-4-yl)carbonyl]pyrrolidin-3-one O-methyloxime, and/or an active metabolite thereof, wherein said compound is administered to a subject in a single dose of 50 mg to 900 mg, more preferably in a single dose of 100 mg to 600 mg.

Whilst a compound of the invention and/or an active metabolite thereof may be used as the sole active ingredient in a medicament, it is also possible for the compound to be used in combination with at least one or more further active compounds. Such further active compounds may be further compounds according to the invention, or other active compounds selected from the group comprising calcium channel blockers, magnesium sulfate, selective prostaglandin modulators, beta-2-adrenergic agonists, beta-3-adrenergic receptor agonists, and/or corticosteroids.

Alternatively, the compound of the invention and/or an active metabolite thereof can be administered concomitantly or separately with at least one compound selected from the group comprising calcium channel blockers (such as nifedipine), magnesium sulfate, prostaglandin receptors modulators (such as agonists or antagonists of either EP1 or EP2 or EP3 or EP4 or FP receptors), prostaglandin synthesis inhibitors (such as indomethacin, nimesulide, sulindac, rofecoxib, celecoxib), beta-2-adrenergic agonists (such as ritodrine, terbutaline, salbutamol), beta-3-adrenergic receptor agonists, nitric acid donors (such as glyceryl trinitrate) and/or corticosteroids (such as dexamethasone, betamethasone).

As used herein, the term "concomitantly" refers to the administration of a compound of formula (3Z,5S)-5-(hydroxymethyl)-1-[(2'-methyl-1,1'-biphenyl-4-yl)carbonyl]pyrrolidin-3-one O-methyloxime, and/or an active metabolite thereof, which is then immediately followed by the administration of at least one compound selected from the group disclosed supra.

As used herein, the term "separately (encompassing sequential or subsequent administration)" refers to the administration of a compound of formula (3Z,5S)-5-(hydroxymethyl)-1-[(2'-methyl-1,1'-biphenyl-4-yl)carbonyl]pyrrolidin-3-one O-methyloxime, and/or an active metabolite thereof, followed by a time period of discontinuance, which is then followed by the administration of at least one compound disclosed supra.

Generally, the compound of the invention is stable in the plasma. As used herein the term "stable" refers to the presence of the compound of formula (3Z,5S)-5-(hydroxymethyl)-1-[(2'-methyl-1,1'-biphenyl-4-yl)carbonyl]pyrrolidin-3-one O-methyloxime, and/or an active metabolite thereof in the plasma of the subject following administration and wherein isomeric interconversion of said compounds is substantially prevented.

Generally, in the present invention the subject in need thereof is preferably a mammal, most preferably a human, more preferably a woman, and most preferably a human female of child bearing age.

The present invention also relates to a compound of formula (3Z,5S)-5-(hydroxymethyl)-1-[(2'-methyl-1,1'-biphenyl-4-yl)carbonyl]pyrrolidin-3-one O-methyloxime, and/or an active metabolite thereof, for use as a medicament.

Also envisioned in the present invention is a compound of formula (3Z,5S)-5-(hydroxymethyl)-1-[(2'-methyl-1,1'-biphenyl-4-yl)carbonyl]pyrrolidin-3-one O-methyloxime, and/or an active metabolite thereof, for use in the treatment and/or prevention of disorders associated with the oxytocin receptor activity and/or vasopressin V1a receptor activity.

The disorders associated with the oxytocin receptor activity and/or vasopressin V1a receptor activity are selected from the non-limiting group comprising preterm labor, premature birth, dysmenorrhea, premature ejaculation, sexual dysfunction, endometriosis, embryo implantation failure due to uterine contractions, infertility, benign prostatic hyperplasia, neuro-psychiatric disorders, autism, social behavior disorders, psycho-social stress, and/or cardiovascular disorders.

The term "preterm labor" referring also to premature labor, shall mean expulsion from the uterus of a viable infant before the normal end of gestation, or more particularly, onset of labor with effacement and dilation of the cervix before the 37th week of gestation. It may or may not be associated with vaginal bleeding or rupture of the membranes.

The term "dysmenorrhea" refers to a condition characterized by cyclic pain associated with menses during ovulatory cycles. The pain is thought to result from uterine contractions and ischemia.

The term "sexual dysfunction" refers to any disturbance or variation in the four phases—excitement phase, plateau phase, orgasmic phase and resolution phase characterizing the human sexual response.

The term "neuro-psychiatric disorders" as used herein refers to mental disorders attributable to diseases of the nervous system, e.g. depression, obsessive-compulsive disorder and others.

The term "social behavior disorders" as used herein refers to emotional disturbance, inappropriate types of behavior or feelings, pervasive mood of unhappiness or depression and a range of perceived difficulties to build or maintain satisfactory interpersonal relationships.

The term "psycho-social stress" as used herein refers to a condition resulting from a perceived threat to the social status, social esteem, self-worth, respect or acceptance within a group, and that lead to development of a stress response in the body and physical symptoms.

Assisted reproduction technologies are methods applied in humans for the treatment of infertility and in animals for producing pregnancies. Infertility, which affects about 10% of human pairs worldwide, may be treated by in vitro fertilization and embryo transfer (IVF-ET) or in less complicated cases, by artificial insemination. Generally, a success of an embryo transfer is dependant on uterine receptivity, an entity that is defined as an ability of uterus to provide optimal conditions mandating proper implantation and embryo development. Basic components of uterine receptivity are uterine contractile activity and the condition of endometrium.

Uterine contractions occurring during the embryo transfer may expel embryos from the uterus towards vagina or oviducts, which may be a cause of unsuccessful treatment, or in latter case a cause of extrauterine pregnancy, a serious, potentially life-threatening complication.

Generally, the present invention relates to a compound of formula (3Z,5S)-5-(hydroxymethyl)-1-[(2'-methyl-1,1'-biphenyl-4-yl)carbonyl]pyrrolidin-3-one O-methyloxime, and/or an active metabolite thereof, for use in assisted reproduction technology.

For example, the present invention relates to a compound of formula (3Z,5S)-5-(hydroxymethyl)-1-[(2'-methyl-1,1'-biphenyl-4-yl)carbonyl]pyrrolidin-3-one O-methyloxime, and/or an active metabolite thereof, for use in the treatment of infertility by in vitro fertilization-embryo transfer (IVF-ET) method.

The present invention also relates to a compound of formula (3Z,5S)-5-(hydroxymethyl)-1-[(2'-methyl-1,1'-biphenyl-4-yl)carbonyl]pyrrolidin-3-one O-methyloxime, and/or an active metabolite thereof, for use in reducing embryo implantation failure due to uterine contractions.

Also envisioned in the present invention is a compound of formula (3Z,5S)-5-(hydroxymethyl)-1-[(2'-methyl-1,1'-biphenyl-4-yl)carbonyl]pyrrolidin-3-one O-methyloxime, and/or an active metabolite thereof, for use in reducing contractions occurring during the embryo transfer.

Furthermore, the present invention relates to a compound of formula (3Z,5S)-5-(hydroxymethyl)-1-[(2'-methyl-1,1'-biphenyl-4-yl)carbonyl]pyrrolidin-3-one O-methyloxime, and/or an active metabolite thereof, for use in the treatment and/or prevention of a disease relating to oxytocin-induced vascular contractility, vasopressin-induced vascular contractility, oxytocin-induced muscular contractility, vasopressin-induced muscular contractility.

The present invention further relates to a pharmaceutical composition comprising a compound of formula (3Z,5S)-5-(hydroxymethyl)-1-[(2'-methyl-1,1'-biphenyl-4-yl)carbonyl]pyrrolidin-3-one O-methyloxime, and/or an active metabolite thereof, and a pharmaceutically acceptable carrier, diluent or excipient.

A "pharmaceutically acceptable carrier, diluent or excipient" used herein is a medium generally accepted in the art for the delivery of biologically active agents to patients. A person skilled in the art is aware of a whole variety of such carriers, diluents or excipients suitable to formulate a pharmaceutical composition (see, for example, Remington's Pharmaceutical Sciences, 18th Ed. Mack Publishing Company, 1990, pp. 1289-1329). The carrier(s), diluent(s) or excipient(s) must be compatible with the other ingredients of the formulation, capable of pharmaceutical formulation, and not deleterious to the recipient thereof.

The compound of the invention and/or an active metabolite thereof, together with a conventionally employed carrier, diluent or excipient may be formulated as pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous) use. Such pharmaceutical compositions and unit dosage forms thereof may comprise ingredients in conventional proportions, with or without additional active compounds or principles, and such unit dosage forms may contain any suitable effective amount of the active ingredient, i.e. the compound of the invention, commensurate with the intended daily dosage range to be employed.

The pharmaceutical compositions of the invention can be administered by a variety of routes including oral, rectal, vaginal, transdermal, subcutaneous, intravenous, intramuscular, and intranasal. Depending on the intended route of delivery, the compounds are preferably formulated as either injectable or oral compositions. The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampoules or syringes of the liquid compositions or pills, tablets, capsules or the like in the case of solid compositions. In such compositions, the compound of the invention is usually a minor component (from about 0.1 to about 50% by weight or preferably from about 1 to about 40% by weight) with the remainder being various vehicles or carriers and processing aids helpful for forming the desired dosing form.

Preferably, the pharmaceutical composition comprising a compound of formula (3Z,5S)-5-(hydroxymethyl)-1-[(2'-methyl-1,1'-biphenyl-4-yl)carbonyl]pyrrolidin-3-one O-methyloxime, and/or an active metabolite thereof, and a pharmaceutically acceptable carrier, diluent or excipient is administered by oral, vaginal or intravenous route.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatine; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as pepper-mint, methyl salicylate, or orange flavoring.

Injectable compositions are typically based upon injectable sterile saline or phosphate-buffered saline or other injectable carriers known in the art.

The compounds of this invention can also be administered in sustained release forms or from sustained release drug delivery systems. A description of representative sustained release materials can also be found in Gennaro, A. R. et al, Remington's Pharmaceutical Sciences. 18th ed. Easton: The Mack Publishing Company, 1995.

The present invention also relates to a process for preparing and isolating the compound of formula (3Z,5S)-5-(hydroxymethyl)-1-[(2'-methyl-1,1'-biphenyl-4-yl)carbonyl]pyrrolidin-3-one O-methyloxime, and/or an active metabolite thereof, in substantially pure form comprising the steps of:
a) Loading a crude isomeric mixture comprising a compound of formula (3Z,5S)-5-(hydroxymethyl)-1-[(2'-methyl-1,1'-biphenyl-4-yl)carbonyl]pyrrolidin-3-one O-methyloxime, and/or an active metabolite thereof, on a gel chromatography column;
b) Purifying with 1% alcohol in organic solvent; and
c) Purifying with 2% alcohol in organic solvent.

As used herein, the term "crude isomeric mixture" refers to a mixture of compounds resulting from the synthesis of a compound of formula (3Z,5S)-5-(hydroxymethyl)-1-[(2'-methyl-1,1'-biphenyl-4-yl)carbonyl]pyrrolidin-3-one O-methyloxime, and/or an active metabolite thereof, as described herein and comprising a compound of formula (3Z,5S)-5-(hydroxymethyl)-1-[(2'-methyl-1,1'-biphenyl-4-yl)carbonyl]pyrrolidin-3-one O-methyloxime and a compound of formula (3E,5S)-5-(hydroxymethyl)-1-[(2'-methyl-1, 1'-biphenyl-4-yl)carbonyl]pyrrolidin-3-one O-methyloxime.

Preferably, the invention relates to a process for preparing and isolating the compound of formula (3Z,5S)-5-(hydroxymethyl)-1-[(2'-methyl-1,1'-biphenyl-4-yl)carbonyl]pyrrolidin-3-one O-methyloxime, and/or an active metabolite thereof, in substantially pure form comprising the steps of:
a) Loading a crude isomeric mixture comprising a compound of formula (3Z,5S)-5-(hydroxymethyl)-1-[(2'-methyl-1,1'-biphenyl-4-yl)carbonyl]pyrrolidin-3-one O-methyloxime, and/or an active metabolite thereof, on a silica gel chromatography column;
b) Purifying with 1% methanol in toluene
c) Purifying with 2% methanol in toluene Preferably, the silica gel chromatography column is chosen from Biotage® Flash 150 flash chromatography system, Biotage KP-SIL, Biotage KP-C18-HS, Biotage KP-C18-WP, Biotage KP-C-WP, Biotage FLASH-WAC 400 (Biotage AB, 751 03 Uppsala, Sweden). Other gel chromatography columns include columns loaded with Mitsubishi Diaion™ HP20 or HP20SS SDVB resins (Mitsubishi Chemical Corporation, Tokyo 100-8251, Japan).

EXAMPLES

Example 1: Purification of (3Z,5S)-5-(hydroxymethyl-1-[(2'-methyl-1,1'-biphenyl-4-yl)carbonyl]pyrrolidin-3-one O-methyloxime 1.1 Synthesis of (3Z/E, 5S)-5-(hydroxymethyl)-1-[((2'-methyl-1,1'-biphenyl-4-yl)carbonyl]pyrrolidin-3-one O-methyloxime The present invention relates to the synthesis and purification of (3Z,5S)-5-(hydroxymethyl)-1-[(2'-methyl-1,1'-biphenyl-4-yl)carbonyl]pyrrolidin-3-one O-methyloxime obtained as a crude isomeric mixture comprising (3Z,5S)-5-(hydroxymethyl)-1-[(2'-methyl-1,1'-biphenyl-4-yl)carbonyl]pyrrolidin-3-one O-methyloxime and (3E,5S)-5-(hydroxymethyl)-1-[(2'-methyl-1,1'-biphenyl-4-yl)carbonyl]pyrrolidin-3-one O-methyloxime.

Synthetic pathways of compounds of the invention are for example those described in WO2004005249 and WO2005082848.

For example, compound of the invention (3Z/E,5S)-5-(hydroxymethyl)-1-[(2'-methyl-1,1'-biphenyl-4-yl)carbonyl]pyrrolidin-3-one O-methyloxime can also be prepared following stages 1 to 7 as described below:

Stage 1: Preparation of 4-(2-methylphenyl)benzoic acid

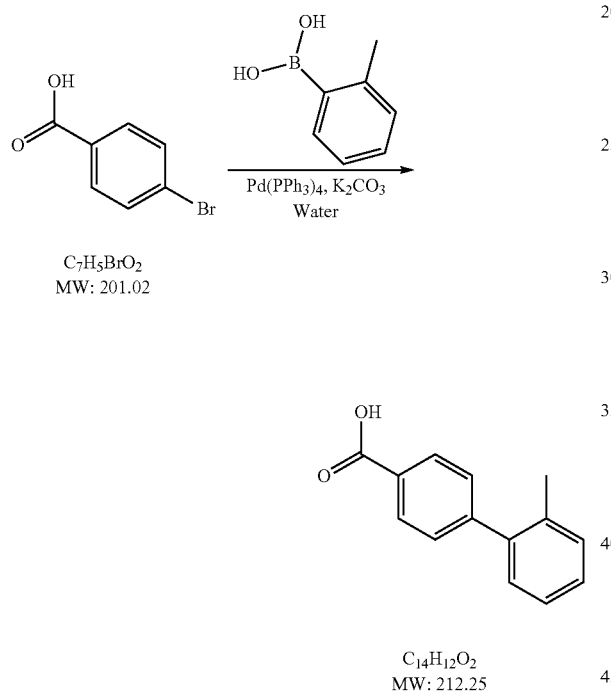

A solution of potassium carbonate (0.908 Kg, 6.57 mol, 2.06 wt) in water (2.20 L, 5.0 vol) was charged to a slurry of 4-bromobenzoic acid (0.441 Kg, 2.19 mol, 1.0 wt) in water (4.41 L, 15.0 vol) at 15 to 25° C. The resulting slurry was stirred at 15 to 25° C. and degassed three times using a vacuum-nitrogen purge cycle. Tetrakis(triphenylphosphine)palladium(0) (0.022 Kg, 0.019 mol, 0.05 wt) was charged and the vacuum-nitrogen purge cycle repeated. A solution of o-tolylboronic acid (0.313 Kg, 2.30 mol, 0.707 wt) in methanol (3.53 L, 8.0 vol) was degassed three times, using a vacuum-nitrogen purge cycle, and then charged to the 4-bromobenzoic acid slurry at 15 to 25° C. The reaction mixture was heated to and maintained at reflux (71 to 78° C.) until reaction completion (The reaction is considered complete at 95% conversion), as determined by ¹H NMR analysis (d6-DMSO), typically 1.5 to 2.5 hours. The reaction mixture was concentrated to 15 vol under vacuum at 40 to 45° C. Toluene (4.41 L, 10.0 vol) and tetrahydrofuran (4.41 L, 10.0 vol) were added to the residue, the resulting mixture stirred vigorously and acidified to pH 1 with hydrochloric acid (6M, 2.00 L, 4.5 vol). The contents were stirred vigorously for 30 to 60 minutes and the layers separated. Toluene (2.20 L, 5.0 vol) and tetrahydrofuran (2.20 L, 5.0 vol) were added to the aqueous phase and the mixture stirred for 5 to 10 minutes. The layers were separated, the combined organic phases filtered and concentrated to 10.0 vol under vacuum at 35 to 40° C. Toluene (4.41 L, 10.0 vol) was added to the residue and the resultant concentrated under vacuum at 35 to 40° C. The tetrahydrofuran content of the resulting slurry was determined by ¹H NMR analysis (d6-DMSO) (Pass level: ≤1.0% w/w tetrahydrofuran with respect to toluene). The slurry was cooled to and aged at O to 5° C. for 30 to 60 minutes, the solid collected by filtration and the filter-cake washed with toluene (2.20 L, 5.0 val). The solid was dried in a vacuum oven at 35 to 40° C. to give 4-(2-methylphenyl)benzoic acid [0.438 Kg, 94.1% th, 99.3% w/w, 1H NMR (d6-DMSO) concordant with structure] as a pale yellow solid.

Stage 2: Preparation of 4-(2-methylphenyl)benzoic acid chloride

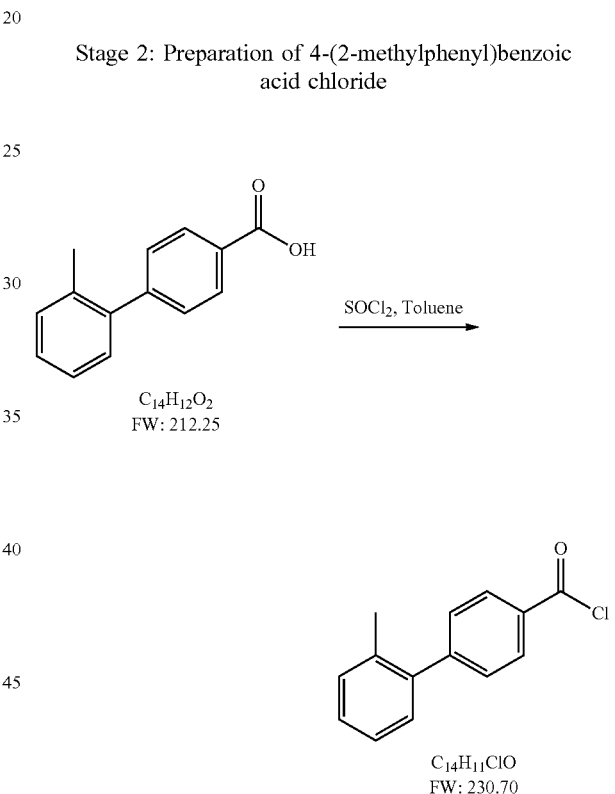

Thionyl chloride (0.300 L, 4.11 mol, 0.685 vol) was added to a slurry of 4-(2-methylphenyl)benzoic acid (0.435 Kg, 2.05 mol, 1.0 wt) in toluene (4.35 L, 10.0 vol) at 10 to 25° C. and the mixture heated to and maintained at 75 to 80° C.3 until complete by 1H NMR analysis (d6-benzene), typically 4 to 5 hours. Reaction completion was accompanied by the formation of a hazy solution. The resultant was concentrated to 5.0 vol by removal of toluene under reduced pressure at 35 to 45° C. Toluene (2.18 L, 5.0 vol) was added to the concentrate and the mixture concentrated to 4.0 vol by removal of toluene under reduced pressure at 35 to 45° C. The resultant was filtered through glass microfibre paper and the filter-cake washed with toluene (0.44 L, 1.0 vol). The toluene solution of 4-(2-methylphenyl)benzoic acid chloride [0.439 Kg, 92.8% th, 100.9% w/w, 1H NMR (d6-benzene) concordant with structure] was used directly in Stage 3.

Stage 3: Preparation of (4R)-4-hydroxy-1-[(2'-methyl-1,1'-biphenyl-4yl)-carbonyl]-L-proline

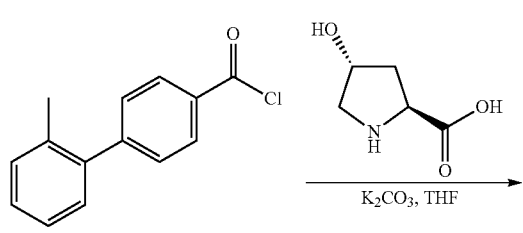

C$_{14}$H$_{11}$ClO
FW: 230.70

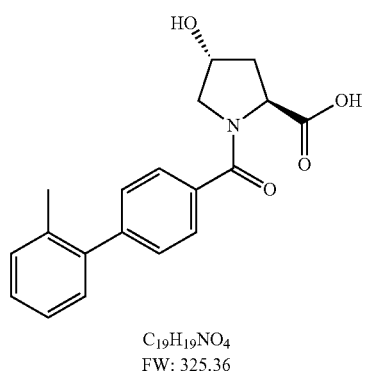

C$_{19}$H$_{19}$NO$_4$
FW: 325.36

A solution of potassium carbonate (0.526 Kg, 3.81 mol, 10.2 wt) in water (O.57 L, 1.3 vol) was charged to a solution of 4-hydroxy-L-proline (0.274 Kg, 2.09 mol, 0.625 wt) in tetrahydrofuran (2.20 L, 5.0 vol) and water (0.44 L, 1.0 vol) at 15 to 25° C. followed by a line rinse of water (0.44 L, 1.0 vol). The mixture was cooled to 0 to 5° C. with rapid stirring and a solution of 4-(2-methylphenyl)benzoic acid chloride (0.438 Kg, 1.90 mol, 1.0 wt) in toluene (2.19 L, 5.0 vol) charged at that temperature followed by a line rinse of toluene (0.44 L, 1.0 vol). The reaction mixture was warmed to 15 to 25° C. over 1 to 2 hours and stirred at this temperature until judged complete by TLC analysis. Water (2.20 L, 5.0 vol) was charged to the reaction mixture at 15 to 25° C. and the layers separated. The aqueous phase was acidified to pH 5 to 6 with aq. hydrochloric acid (6M, 0.66 L, 1.5 vol) and then to pH with aq. hydrochloric acid (2M, 0.88 L, 2.0 vol) at 15 to 25° C. The mixture was cooled to and aged at 0 to 5° C. for 30 to 60 minutes, the precipitated solid collected by filtration, the filter-cake washed with water (2×1.75 L, 2×4.0 vol) and toluene (0.88 L, 2.0 vol) and pulled dry on the filter for 12 to 24 hours. The collected solid was dried under vacuum at 40 to 45° C. until the water content by KF was ≤0.2% w/w to afford (4R)-4-hydroxy-1-[(2'-methyl-1,1'-biphenyl-4-yl)carbonyl]-L-proline [0.599 Kg, 97.0% th, 136.8% w/w, $^1$H NMR (d$_6$-DMSO) concordant with structure] as an off-white solid.

Stage 4: Preparation of 1-(2'-methyl-1,1'-biphenyl-4-yl)carbonyl-4-oxo-L-proline

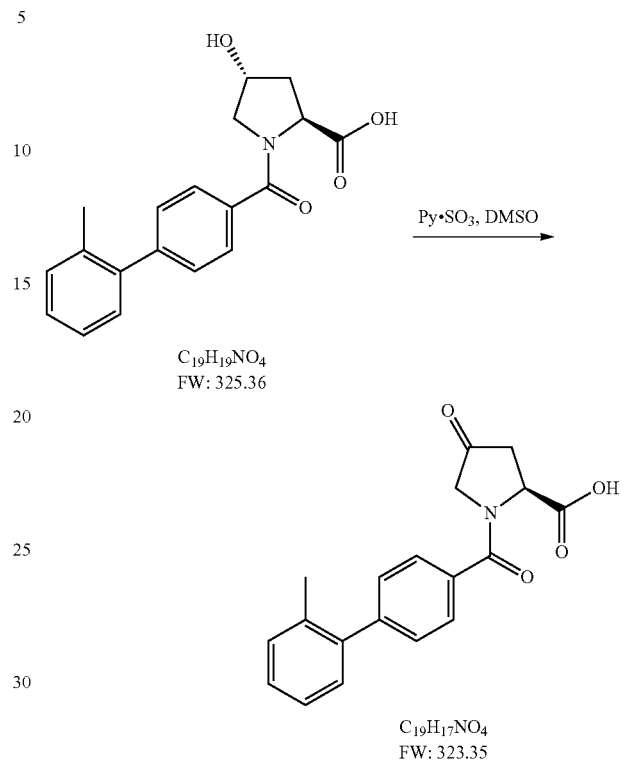

Triethylamine (1.80 L, 13.56 mol, 3.0 vol) was charged to a solution of (4R)-4-hydroxy-1-[(2'-methyl-1,1'-biphenyl-4-yl)carbonyl]-L-proline (0.598 Kg, 1.84 mol, 1.0 wt) in dimethyl sulfoxide (4.42 L, 7.4 vol) at 15 to 20° C. Pyridine-sulphur trioxide complex (0.879 Kg, 5.52 mol, 1.47 wt) was charged portion-wise at 15 and 25° C. and the reaction mixture stirred at that temperature until reaction completion, as determined by TLC analysis (typically 1 to 3 hours). 7 The reaction was quenched with aq. hydrochloric acid (3M, 4.80 L, 8.0 vol) at 0 to 30° C., tetrahydrofuran (3.00 L, 5.0 vol) and heptanes (0.60 L, 1.0 vol) charged, the layers separated and the aqueous phase extracted with tetrahydrofuran (2×3.00 L, 2×5.0 vol). The combined organic phases were washed with aq. hydrochloric acid (1 M, 2×1.20 L, 2×2.0 vol) and saturated sodium chloride solution (2×1.20 L, 2×2.0 vol), the aqueous washes combined and back-extracted with tetrahydrofuran (2×0.60 L, 2×1.0 vol). The combined organics were dried over magnesium sulphate (1.794 Kg, 3.0 wt), filtered, the filtercake washed with tetrahydrofuran (0.60 L, 1.0 vol) and the filtrates concentrated under vacuum at 40 to 45° C. to give a pale brown foam. Ethyl acetate (6.00 L, 10.0 vol) was charged to the foam, the contents stirred for 5 to 10 minutes to reach dissolution and the solvent removed under vacuum at 40 to 45° C. This was repeated using ethyl acetate (6.00 L, 5.0 vol) until tetrahydrofuran was not detected by $^1$H NMR analysis (d$_6$-DMSO). The residue was slurried in ethyl acetate (4.80 L, 8.0 vol), activated carbon (0.084 Kg, 0.14 wt) added followed by a line rinse of ethyl acetate (3.00 L, 5.0 vol), the resultant heated to and maintained at 70 to 80° C. for 20 to 30 minutes, cooled to 40 to 55° C. and filtered through glass microfibre paper. The filter-cake was washed with ethyl acetate (1.50 L, 2.5 vol) and the combined filtrates and wash concentrated to 2.5 to 3.5 vol under vacuum at 40 to 45° C. Crystallisation commenced during the concentration. The concentrate was transferred to a suitable vessel with a line rinse of ethyl acetate (0.30 L, 0.5 vol) and heated to 70 to 80° C. Additional ethyl acetate (0.30 L 0.5 vol) was added as necessary to achieve dissolution. Heptanes (1.80 L, 3.0 vol) was added at 70 to 80° C. and the contents allowed to cool to between 15 and 25° C. over 1 to 2 hours. The slurry was further cooled to and aged at 0 to 5° C. for 2 to 3 hours, filtered and the filtercake washed with ethyl acetate:heptanes (1:1, 0.60 L, 1.0 vol) at 0 to 5° C. followed by heptanes (3.0 L, 2.5 vol). The collected solid was dried under vacuum at 40 to 45° C. to give 1-[(2'-methyl-1,1'-biphenyl-4-yl)carbonyl]-4-oxo-L-proline [0.444 Kg, 74.7% th, 74, 2% w/w, $^1$H NMR (d6-DMSO) concordant with structure] as an off-white solid.

Stage 5: Preparation of (4Z/E)-4-methoxyimino-1-[(2'-methyl-1,1'-biphenyl-4-yl)carbonyl]-L-proline washed with aq. hydrochloric acid (1 M, 2×2.20 L, 2×5.0 vol). The acidic washes were back extracted with ethyl acetate (2.20 L, 5.0 vol), the combined organic phases washed with sat. aq. sodium chloride solution (3.10 L, 7.0 vol), dried over magnesium sulfate (0.300 Kg, 0.69 wt), filtered and the filtercake washed with ethyl acetate (2.20 L, 5.0 vol). The filtrate and washes were combined and concentrated under vacuum at 35 to 40° C. to afford 4-methoxyimino-1-[(2'-methyl-1,1'-biphenyl-4-yl)carbonyl]-L-proline [0.476 Kg, 100.6% th, 109.6% w/w, $^1$H NMR (CDCl$_3$) concordant with structure] as an off-white solid.

Stage 6: Preparation of (4Z/E, 2S)-methyl-1-[(2'-methyl-1,1'-biphenyl-4-yl)-carbonyl]-4-methoxy-imino pyrrolidine-2-carboxylate

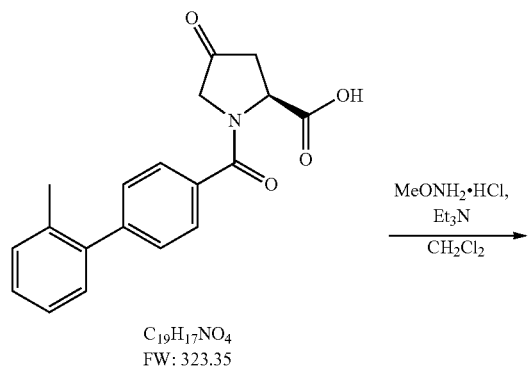

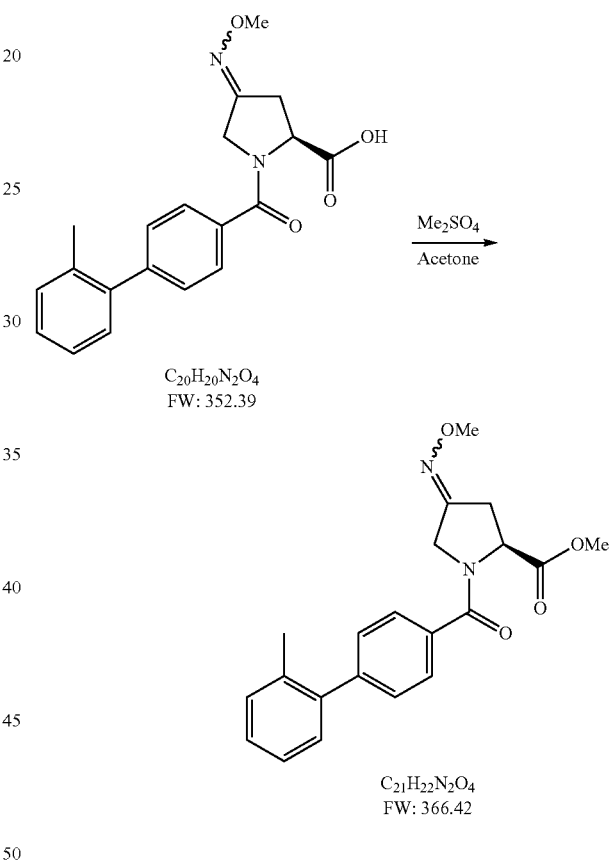

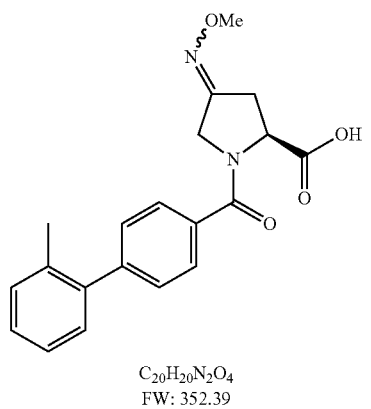

Triethylamine (0.40 L, 2.85 mol, 0.92 vol) was added to a solution of 1-[(2'-methyl-1,1'-biphenyl-4-yl)carbonyl]-4-oxo-L-proline (0.434 Kg, 1.34 mol, 1.0 wt) in dichloromethane (4.40 L, 10.0 vol) at 10 to 25° C. followed by a line rinse of dichloromethane (0.43 L, 1.0 vol). Methoxylamine hydrochloride (0.130 Kg, 1.56 mol, 0.30 wt) was added portionwise at 10 to 25° C. followed by a line rinse of dichloromethane (0.43 L, 1.0 vol) and the reaction mixture stirred at 10 to 25° C. until reaction completion, as determined by TLC analysis (typically 3 to 5 hours. TLC eluent: dichloromethane:methanol:acetic acid (90:10:1); uv visualization). The solvent was removed under vacuum at 35 to 40° C., the resultant dissolved in ethyl acetate (4.40 L, 10.0 vol) and Potassium carbonate (0.476 Kg, 3.44 mol, 1.0 wt) was added to a solution of 4-methoxyimino-1-[(2'-methyl-1,1'-biphenyl-4-yl)carbonyl]-L-proline (0.475 Kg, 1.35 mol, 1.0 wt) in acetone (4.75 L, 10.0 vol) and the mixture cooled to 0 to 10° C. Dimethyl sulfate (0.128 L, 1.35 mol, 0.27 vol) was added at 0 to 15° C. and the mixture stirred at 15 to 25° C. until reaction completion, as determined by TLC analysis, typically 3 to 16 hours. The solvent was removed under vacuum at 40 to 45° C. and the resultant partitioned between ethyl acetate (3.80 L, 8.0 vol) and water (3.80 L, 8.0 vol). The layers were separated, the organic phase washed with sat. aq. sodium chloride solution (2.85 L, 6.0 vol), dried over sodium sulfate (0.953 Kg, 2.0 wt) and filtered. The filtercake was washed with ethyl acetate (0.48 L, 1.0 vol) and the combined filtrate and wash concentrated under vacuum at 40 to 45° C. Excess ethyl acetate was removed by azeotropic distillation with tetrahydrofuran (2×0.95 L, 2×2.0 vol) under vacuum at 40 to 45° C. to give (4Z/E, 2S)-methyl-1-[(2'-methyl-1,1'-biphenyl-4-yl)-carbonyl]-4-methoxyimino pyrrolidine-2-carboxylate [0.492 Kg, 99.6% th, 103.6% w/w, $^1$H NMR (CDCl$_3$) concordant with structure] as a viscous brown oil.

Stage 7: Preparation of (3Z/E,5S)-5-(hydroxymethyl)-1-[(2'-methyl-1,1'-biphenyl-4-yl)carbonyl]pyrrolidin-3-one O-methyloxime

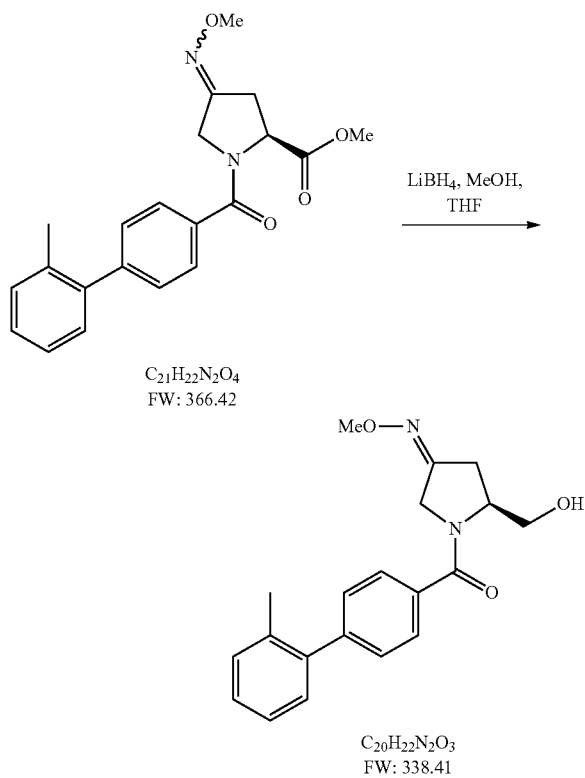 [SMILES: CON=C1C[C@@H](C(=O)OC)N(C(=O)c2ccc(-c3ccccc3C)cc2)C1 ; CO/N=C1/C[C@@H](CO)N(C(=O)c2ccc(-c3ccccc3C)cc2)C1]

C$_{21}$H$_{22}$N$_2$O$_4$
FW: 366.42

LiBH$_4$, MeOH, THF

C$_{20}$H$_{22}$N$_2$O$_3$
FW: 338.41

Lithium borohydride (0.049 Kg, 2.26 mol, 0.1 wt) was added portionwise under nitrogen to a stirred solution of (4Z/E, 2S)-methyl-1-[(2'-methyl-1,1'-biphenyl-4-yl)-carbonyl]-4-methoxyimino pyrrolidine-2-carboxylate (0.492 Kg, 1.34 mol, 1.0 wt) in tetrahydrofuran (2.31 L, 4.7 vol) and methanol (2.31 L, 4.7 vol) at 0 to 30° C. The mixture was stirred at 15 to 25° C. to reaction completion, as determined by TLC analysis (Eluent: ethyl acetate; Visualisation: ninhydrin), typically 2 to 6 hours. The reaction mixture was quenched with water (0.40 L, 0.8 val) at 15 to 25° C. and stirred at 15 to 25° C. for 16 to 20 hours. The resultant was concentrated under vacuum at 40 to 45° C. and the residue partitioned between water (2.46 L, 5.0 vol) and ethyl acetate (4.92 L, 10.0 vol). The layers were separated, the organic phase washed sequentially with aq. hydrochloric acid (1M, 2.46 L, 5.0 vol), sat. aq. sodium hydrogen carbonate solution (2.46 L, 5.0 vol) and sat. aq. sodium chloride solution (2.46 L, 5.0 vol). The organic phase was dried over magnesium sulfate (0.985 Kg, 2.0 wt), filtered and the filter-cake washed with ethyl acetate (0.50 L, 1.0 vol). The combined filtrate and wash were concentrated under vacuum to give a crude isomeric mixture comprising (3Z/5S)-5-(hydroxymethyl)-1-[(2'-methyl-1,1'-biphenyl-4-yl)carbonyl]pyrrolidin-3-one O-methyloxime and (3E,5S)-5-(hydroxymethyl)-1-[(2'-methyl-1,1'-biphenyl-4-yl)carbonyl]pyrrolidin-3-one O-methyloxime [0.395 Kg, 86.9% th, 80.3% w/w, 1H NMR (CDCl$_3$) concordant with structure; 82.0% area by HPLC, 71.4:28.6 Z/E ratio] as a viscous brown oil. The oil was dissolved in toluene (0.40 L, 1.0 vol, with respect to weight of product) and stored until required.

1.2 Dry Flash Chromatography of Crude (31/E,5S)-5-(hydroxymethyl)-1-[(2'-methyl-1,1'-biphenyl-4-yl)carbonyl]pyrrolidin-3-one O-methyloxime A dry flash chromatography purification of the crude isomeric mixture obtained following the protocol described above was attempted using different elution conditions. A crude mixture of (3Z/E,5S)-5-(hydroxymethyl)-1-[(2'-methyl-1,1'-biphenyl-4-yl)carbonyl]pyrrolidin-3-one O-methyloxime concentrated to dryness was re-dissolved in 2 volume toluene and loaded onto a pad of SiO2 (5 wt) prior to elution using 25 volume fractions of eluent.

Fractions 1-5: eluted with pure toluene
Fractions 6-10: eluted with Toluene/MeOH 1% vol/vol
Fractions 10 to 15: eluted with Toluene/MeOH 2% vol/vol The Z and E forms are shown by shaded spots. Fractions 8 to 13 were combined and concentrated to dryness. The results show a recovery of 75%. There was no improvement in the E/Z ratio. A minor gain of about 4% area in purity of the isomeric mixture (E+Z) was observed before and after dry-flash chromatography (Table I).

TABLE I

Comparative impurity profile before and after dry-flash chromatography

| | % area | | | |
|---|---|---|---|---|
| | Impurity at RRT 0.7 | E + Z-isomers | Impurity at RRT 1.08 | RRT 1.12 (Ar—Ar—CH2OH) |
| Before dry flash | 4.6 | 91.3 | <0.5 | 4.1 |
| After dry-flash | 2.5 | 95.6 | <0.5 | 0.7 |

RRT: Relative retention time

The dry-flash chromatography of the crude isomeric mixture does not allow the purification of (3Z,5S)-5-(hydroxymethyl)-1-[(2'-methyl-1,1'-biphenyl-4-yl)carbonyl]pyrrolidin-3-one O-methyloxime. The E/Z ratio pre and post dry-flash remain in the range of 30/70 to 40/60.

Furthermore, such an approach should be considered on the basis of the scale at which the operation has to be carried out. On a 20 L scale, this operation would not be a time saving approach.

1.3 Assessment Toward Crystallization of the Pure Z from the Crude Isomeric Mixture The first part of the assessment toward crystallisation of the pure (3Z,5S)-5-(hydroxymethyl)-1-[(2'-methyl-1,1'-biphenyl-4-yl)carbonyl]pyrrolidin-3-one O-methyloxime from the crude mixture (3Z/E,5S)-5-(hydroxymethyl)-1-[(2'-methyl-1,1'-biphenyl-4-yl)carbonyl]pyrrolidin-3-one O-methyloxime, has been looking at solubility and possible crystallisation conditions of the pure (3Z,5S)-5-(hydroxymethyl)-1-[(2'-methyl-1,1'-biphenyl-4-yl)carbonyl]pyrrolidin-3-one O-methyloxime. The results of the solubility/crystallisation tests carried out on 15 mg scale are reported in Table II below

TABLE II

Qualitative solubility data for (3Z,5S)-5-(hydroxymethyl)-1-[(2'-methyl-1,1'-biphenyl-4-yl)carbonyl]pyrrolidin-3-one O-methyloxime

| Solvent | Dissolves in: | Comment |
|---|---|---|
| heptanes | — | insoluble in 20 vol |
| toluene | 2 vol cold | |
| DIPE | 40 vol hot | |
| THF | 4 vol cold | |
| tBuOH | 6 vol hot | |
| MIBK | 4 vol hot | |
| IPA | 4 vol hot | |

The initial solubility screen showed that pure (3Z,5S)-5-(hydroxymethyl)-1-[(2'-methyl-1,1'-biphenyl-4-yl)carbonyl]pyrrolidin-3-one O-methyloxime isomer is soluble in a range of solvents. On the basis of the above results, crystallisation by addition of anti-solvent was examined and the results reported in Table HIII. The anti-solvent was added to a warm solution ca 40-50° C. and allowed to cool to room temperature.

In particular, the water (anti-solvent) was added to a warm (40-50° C.) solution of (3Z,5S)-5-(hydroxymethyl)-1-[(2'-methyl-1,1'-biphenyl-4-yl)carbonyl]pyrrolidin-3-one O-methyloxime in IPA until cloudiness was reached and the mixture was allowed to cool to room temperature.

TABLE III

Crystallisation via addition of anti-solvent

| Solvent | Antisolvent | Comment |
|---|---|---|
| toluene 20 vol | heptanes 39 vol | oils out |
| THF 10 vol | heptanes 40 vol | oils out |
| tBuOH 10 vol | water 20 vol | oils out |
| MIBK 10 vol | heptanes 40 vol | oils out |
| IPA 20 vol | water 160 vol | very fine solid, oils out on standing |
| IPA 8 vol | water 18 vol | very fine solid, oils out on standing |
| DMSO 10 vol | water 12 vol | gel |
| NMP 10 vol | water 28 vol | oils out |
| MeOH 10 vol | water 10 vol | oils out |
| DMSO 20 vol | water 16 vol | oils out |
| acetone 10 vol | water 10 vol | oils out |
| DCM 10 vol | heptanes 50 vol | oils out |

The IPA/water crystallisation conditions were applied to a crude isomeric mixture. The toluene solution was first concentrated to dryness prior to dissolution in IPA (8 vol) and addition of water (18 vol). Unfortunately, this resulted in material de-mixing as oil.

In another experiment, the antisolvent was added to a solution of crude (3Z,5S)-5-(hydroxymethyl)-1-[(2'-methyl-1,1'-biphenyl-4-yl)carbonyl]pyrrolidin-3-one O-methyloxime (90.4% area purity, contained 0.5% w/w toluene and 3.7% w/w THF) at room temperature until cloudiness was reached and the mixture was left to stand at room temperature (Table IV).

TABLE IV

Crystallisation by addition of water at 18-22° C.

| Solvent | Antisolvent | Comment |
|---|---|---|
| MeOH 5 vol | water 3 vol | oils out |
| DMSO 5 vol | water 3 vol | oils out |

At this point of the investigation, no suitable conditions of crystallisation of the pure (3Z,5S)-5-(hydroxymethyl)-1-[(2'-methyl-1,1'-biphenyl-4-yl)carbonyl]pyrrolidin-3-one O-methyloxime or allowing isolation of solid containing (3Z,5S)-5-(hydroxymethyl)-1-[(2'-methyl-1,1'-biphenyl-4-yl)carbonyl]pyrrolidin-3-one O-methyloxime have been identified.

Further crystallisation attempts were carried out using crude isomeric mixture of (3Z/E,5S)-5-(hydroxymethyl)-1-[(2'-methyl-1,1'-biphenyl-4-yl)carbonyl]pyrrolidin-3-one O-methyloxime. In all cases, the volume of solvents was smaller than what used previously and based only on a single solvent. The crude material (E/Z ratio 33:67 and purity (E+Z) 79.52% area) used for this crystallisation was concentrated to a foam (Table V).

TABLE V crystallisation from single solvent at lower volume

| Material | Solvent | Ageing in freezer | Ageing in fridge |
|---|---|---|---|
| 'Pure Z' | Ethyl Acetate 1.8 vol | Crystallises re-dissolves as warms | Stays in solution, with and without seeding after 2 days. |
| Crude | | Does not crystallize with or without seeding. | n/a |
| 'Pure Z' | Diethylether 2.3 vol | On addition of ether at 18-22° C. starts to dissolve then crashes out again. Recovery 70% Used for seeding | n/a |
| Crude | | Oils Re-dissolves as warms | Crystallises recovery 41% E/Z ratio 40/60 purity 85.4% area. (mother liquors E/Z ratio 20/80 purity 62.1% area). Seeds not used. |
| 'Pure Z' | TBME 2.3 vol | Oils Re-dissolves as warms | Stays in solution, with and without seeding after 2 days. |
| Crude | | Oils Re-dissolves as warms | Stays in solution, with and without seeding after 2 days. |

Crystallisation using ethyl acetate followed by aging in a freezer overnight gave crystallisation using the pure (3Z,5S)-5-(hydroxymethyl)-1-[(2'-methyl-1,1'-biphenyl-4-yl)carbonyl]pyrrolidin-3-one O-methyloxime material, but quickly re-dissolved as the sample warmed. No crystals were observed using crude material in ethyl acetate even when seeds were added.

Crystallisation using diethylether followed by aging in a fridge gave crystallisation using the crude (3Z/E,5S)-5-(hydroxymethyl)-1-[(2'-methyl-1,1'-biphenyl-4-yl)carbonyl]pyrrolidin-3-one O-methyloxime material. The solid was collected in 41% recovery. Unfortunately, the collected solid had a slighter poorer E/Z ratio than the input material and a slightly higher chemical purity.

TBME as solvent for both pure Z and crude gave oiling after aging in freezer, and stayed in solution after aging in the fridge with and without seeds.

Suitable crystallization conditions of the crude isomeric mixture allowing improvement of the Z/E ratio and of the purity of the isomeric mixture (E+Z) have not been found.

1.4 Substantially pure form of (3Z,5 S)-5-(hydroxymethyl)-1-[(2'-methyl-1,1'-biphenyl-4-yl)carbonyl]pyrrolidin-3-one O-methyloxime 1.4.1 Small Scale Purification The isolation procedure in substantially pure form of (3Z,5S)-5-(hydroxymethyl)-1-[(2'-methyl-1,1'-biphenyl-4- yl)carbonyl]pyrrolidin-3-one O-methyloxime was performed by chromatography using a Biotage system (Biotage AB, SE-751 03 Uppsala, Sweden) of the crude isomeric mixture isolated after reduction of the oxime ester (Stage 7 of Example 1).

Five distinct batches (No. 020, 180, 062, 068, 076) of the crude isomeric mixture were purified by Biotage chromatography. Furthermore, different conditions were used regarding batches No. 068 and 076. Purification was performed with a 5% w/w spike of oxime methyl ester added (No. 068), and with an overloaded Biotage column (No. 076).

Each chromatography was run using Biotage 40M cartridges (40 g silica) which had been pre-flushed with toluene. Toluene:MeOH (99:1 v/v) was then eluted and collected in 100 ml fractions (total volume 4 L), followed by a flush of toluene:MeOH (96:4 v/v).

Fractions were analysed by TLC (eluent: ethylacetate) to determine which fractions could be discarded and which fractions contained Z isomer. These Z fractions were then analyzed by HPLC. The pass criteria for a fraction was >96% Z isomer and <1.2% E isomer.

Surprisingly, the purification through Biotage chromatography of various batches was very efficient as the substantially pure form of (3Z,5S)-5-(hydroxymethyl)-1-[(2'-methyl-1,1'-biphenyl-4-yl)carbonyl]pyrrolidin-3-one O-methyloxime is purified at 99.4% (Batches No. 020, No. 062, No. 068) and at 99.2% (Batches No. 180, No. 076). In particular, the Biotage chromatography in presence of oxime ester removes 5% w/w oxime ester without detriment to recovery or quality (Batch No. 068) and a 25% overcharge of the Biotage column does not cause a decrease in yield or quality (batch No. 076).

TABLE VI efficiency of the Biotage chromatography

| Batch No. | Input % E/Z | Output % E/Z | yield of Z isomer |
|---|---|---|---|
| 020 | 3.0 g<br>85.7% area purity<br>% E/Z: 30.5/69.5 | Pure Z-fractions:<br>1.0 g<br>98.8% area purity<br>% E/Z: 0.6/99.4 | 33% |
| 180 | 2.0 g<br>92.0% area purity<br>% E/Z: 32.8/67.2 | Pure Z-fractions<br>0.9 g<br>99.6% area purity<br>% E/Z: 0.8/99.2 | 45% |
| 062 | 3.0 g<br>83.5% area purity<br>% E/Z: 32.7/67.3 | Pure Z-fractions<br>1.3 g<br>99.8% area purity<br>% E/Z: 0.6/99.4 | 43% |
| | | Mixture:<br>1.2 g<br>91.0% area purity<br>% E/Z: 69.6/30.4 | 11% |
| 068 | 3.0 g spiked with ~5% ester<br>~78% area purity<br>% E/Z: 32.7/67.3 | Pure Z fractions:<br>1.2 g<br>99.8% area purity<br>% E/Z: 0.6/99.4 | 40% |
| | | Mixture:<br>0.6 g<br>98.8% area purity<br>% E/Z: 27.9/72.1 | 14% |
| | | Pure E fractions:<br>1.1 g<br>70.7% area purity<br>% E/Z: 98.7/1.3<br>(19.3% ester) | N/A |
| 076 | 3.8 g<br>83.5% area purity<br>% E/Z: 32.7/67.3 | Pure Z fractions<br>1.4 g<br>99.8% area purity<br>% E/Z: 0.8/99.2 | 37% |
| | | Mixture:<br>1.8 g<br>95.0% area purity<br>% E/Z: 63.6/36.4 | 17% |

1.4.2 Large Scale Purification

Various batches of crude (3Z/E,5S)-5-(hydroxymethyl)-1-[(2'-methyl-1,1'-biphenyl-4-yl)carbonyl]pyrrolidin-3-one O-methyloxime (0.392 kg, 1.16 mol, 1.0 wt) were charged to a Biotage 150 L SIM unit as an approximate 50% w/w solution in toluene and purified using 1% methanol in toluene (150 L) followed by 2% methanol in toluene (50 L), fraction size 5.0 L. The collected fractions were analysed by TLC[15] and HPLC analyses, as appropriate. The fractions that were deemed to contain clean (3Z,5S)-5-(hydroxymethyl)-1-[(2'-methyl-1,1'-biphenyl-4-yl)carbonyl]pyrrolidin-3-one O-methyloxime (criteria: Z-isomer≥96.00% area, E-isomer≤1.20% area) were combined and concentrated under vacuum at 40 to 45° C. Absolute ethanol (2×2 L) was added to the residue and the solution concentrated under vacuum at 40 to 45° C. until the foamy solid could be manipulated. The desired product, (3Z,5S)-1-[(biphenyl-4-yl-carbonyl)-5-hydroxy-methyl]pyrrolidine-3-one-O-methyloxime (0.089 Kg, 22.7% w/w, $^1$H NMR (CDCl$_3$) concordant with structure, 99.3% area by HPLC, 98.4:0.9 Z/E ratio was obtained as an off-white to light brown solid.

TABLE VII

Summary of purification of different batches of (3Z,5S)-5-(hydroxymethyl)-1-[(2'-methyl-1,1'-biphenyl-4-yl)carbonyl]pyrrolidin-3-one O-methyloxime in substantially pure form.

| Batch No. | Input (kg) | Output (kg) | Yield (% w/w) | % Z form (% area) | % E form (% area) |
|---|---|---|---|---|---|
| 12 | 0.392 | 0.089 | 22.8 | 98.65 | 0.85 |
| 116 | 0.392 | 0.114 | 29 | 98.34 | 0.89 |
| 120 | 0.441 | 0.081 | 18.4 | 97.90 | 1.81 |
| 122 | 0.380 | 0.094 | 24.3 | 98.52 | 1.14 |
| 124 | 0.387 | 0.096 | 25.3 | 98.89 | 0.73 |
| 126 | 0.390 | 0.132 | 33.8 | 98.40 | 0.95 |
| 128 | 0.526 | 0.010 | 2 | 98.20 | 0.83 |
| 130 | 0.453 | 0.086 | 19 | 98.46 | 1.23 |
| 132 | 0.440 | 0.082 | 19.3 | 98.86 | 0.85 |
| 134 | 0.39 | 0.144 | 36.9 | 98.73 | 0.96 |
| 138 | 0.273 | 0.098 | 35.9 | 98.92 | 0.66 |
| 140 | 0.463 | 0.059 | 13.1 | 98.52 | 1.13 |
| 142 | 0.462 | 0.084 | 18.4 | 99.37 | 0.48 |
| 144 | 0.442 | 0.126 | 29 | 99.1 | 0.68 |
| 146 | 0.409 | 0.135 | 33.5 | 99.21 | 0.46 |
| 148 | 0.460 | 0.107 | 23.8 | 99.13 | 0.65 |
| 150 | 0.409 | 0.071 | 18 | 98.92 | 0.66 |
| 152 | 0.392 | 0.054 | 14.3 | 98.82 | 0.76 |
| 156 | 0.445 | 0.039 | 8.8 | 98.64 | 0.87 |
| 158 | 0.392 | 0.06 | 15.3 | 98.73 | 0.63 |
| 162 | 0.435 | 0.150 | 34.5 | 98.94 | 0.79 |
| 164 | 0.434 | 0.192 | 44.2 | 99.21 | 0.58 |
| 166 | 0.415 | 0.074 | 17.8 | 98.79 | 0.73 |
| 174 | 0.518 | 0.108 | 20.8 | 99.11 | 0.64 |
| 176 | 0.342 | 0.072 | 21 | 98.88 | 0.77 |

TABLE VII-continued

Summary of purification of different batches of (3Z,5S)-5-(hydroxymethyl)-1-[(2'-methyl-1,1'-biphenyl-4-yl)carbonyl]pyrrolidin-3-one O-methyloxime in substantially pure form.

| Batch No. | Input (kg) | Output (kg) | Yield (% w/w) | % Z form (% area) | % E form (% area) |
|---|---|---|---|---|---|
| 178 | 0.415 | 0.074 | 17.8 | 99.07 | 0.71 |
| 180 | 0.353 | 0.174 | 49.3 | 99.03 | 0.82 |
| 182 | 0.270 | 0.178 | 65.9 | 99.10 | 0.53 |

Appropriate batches of (3Z,5S)-5-(hydroxymethyl)-1-[(2'-methyl-1,1'-biphenyl-4-yl)carbonyl]pyrrolidin-3-one O-methyloxime (2.713 kg, 1.0 wt) isolated from the Biotage chromatography were combined and dissolved in absolute ethanol (5.16 L, 2.0 vol) at 15 to 25° C., clarified by filtration through glass microfibre paper and an absolute ethanol wash (0.50 L, 0.2 vol) applied to the filter. The combined filtrates were concentrated portion wise under vacuum at 40 to 45° C. The resultant was transferred to drying trays and dried under vacuum at 30° C. for 24 hours. The oven temperature was then increased incrementally from 30 to 40° C. over 80 hours. The level of residual solvent was determined by $^1$H NMR analysis (CDCl$_3$) and when found to be <1.0% w/w the solid was passed through a 500 μm aperture sieve. The solid was returned to the oven and dried at 40 to 42° C. until the solvent level was ≤0.40% w/w to afford (3Z,5S)-1-[(biphenyl-4-yl-carbonyl)-5-hydroxy-methyl]-pyrrolidine-3-one-O-methyloxime (2.633 Kg, 97.1% w/w, 1H NMR (CDCl3) concordant with structure, 98.65% area by HPLC.

The combination procedure is summarized below:
Input: 2.713 kg
Output: 2.633 kg
Yield: 97.1% w/w Example 2: (3Z,5S)-5-(hydroxymethyl)-1-[(2'-methyl-1,1'-biphenyl-4-yl)carbonyl]pyrrolidin-3-one O-methyloxime binding to OT-R and Vasopressin V1a Receptor Binding to the OT-R and Vasopressin V1a Receptor Competition binding to the human oxytocin receptor was measured in vitro using a scintillation proximity assay.

This assay allows determining the affinity of the test compounds for OT-R. Membranes from HEK293EBNA (cells expressing OT-R) were suspended in buffer containing 50 mM Tris-HCl, pH 7.4, 5 mM MgCl2 and 0.1% BSA (w/v). The membranes (2-4 μg) were mixed with 0.1 mg SPA bead coated with wheat-germ aglutinin (WGA-PVT-Polyethylene Imine beads from Amersham) and 0.2 nM of the 125 radiolabelled [I]-OVTA (OVTA being Ornithin Vasoactive, an analogue of OT for competitive binding experiments). Non-specific binding was determined in the presence of 1 μM Oxytocin. The total assay volume was 100 μl. The plates (Corning® NBS plate) were incubated at room temperature for 30 min and counted on a Mibrobeta® plate scintillation counter. Competitive binding was performed in presence of compounds of the present invention at the following concentrations: 30 μM, 10 μM, 1 μM, 300 nM, 100 nM, 10 nM, 1 nM, 100 pM, 10 pM. The competitive binding data were analysed using the iterative, nonlinear, curve-fitting program, "Prism" (GraphPad Software, Inc).

The ability of the compounds of the present invention to inhibit the binding of I-OVTA to the OT-receptor was assessed using the above described in vitro biological assay. The binding affinity of test compounds from the above examples is expressed by the inhibition constant (Ki; nM). From these values, it can be derived that said test compounds according to the present invention do show a significant binding to the oxytocin receptor.

The inhibition constant Ki of (3Z,5S)-5-(hydroxymethyl)-1-[(2'-methyl-1,1'-biphenyl-4-yl)carbonyl]pyrrolidin-3-one O-methyloxime to the oxytocin receptor is Ki (nM)=52 nM and to the vasopressin V a receptor is Ki (nM)=120 nM. Thus (3Z,5S)-5-(hydroxymethyl)-1-[(2'-methyl-1,1'-biphenyl-4-yl)carbonyl]pyrrolidin-3-one O-methyloxime is selective for the oxytocin receptor.

Example 3: (3Z,5S)-5-(hydroxymethyl)-1-[(2'-methyl-1'-biphenyl-4-yl)carbonyl]pyrrolidin-3-one O-methyloxime is a OT-R Antagonist The inhibition of oxytocin-induced Ca2+ mobilization in OT-R transfected HEK293EBNA cells was measured by FLIPR (fluorimetric imaging plate reader).

This assay allows the measurement of the inhibition of OT/OT-R mediated calcium mobilization by the compound (3Z,5S)-5-(hydroxymethyl)-1-[(2'-methyl-1,1'-biphenyl-4-yl)carbonyl]pyrrolidin-3-one O-methyloxime.

FLIPR® is a fluorimetric imaging device using a laser (Argon-ion laser) for simultaneous illumination and reading (cooled CCD camera) of each well of a 96-well-plate, thus enabling rapid measurements on a large number of samples.

Preparing the plates: FLIPR-plates were pre-coated with PLL (Poly-L-Lysine) 10 μg/ml+0.1%) gelatine to attach HEK293EBNA cells (Human Embryonic Kidney cells expressing OT-R) and incubated for 30 min up to 2 days at 37° C. The cells were plated out into 96-well-plates (60000 cells/well).

Labelling with fluo-4: 50 μg of Fluo-4 (Ca2+ sensitive fluorescent dye) were dissolved in 20 μl pluronic acid (20% in DMSO). The dissolved fluo-4 was then diluted in 10 ml DMEM (Dubecco's Minimal Essential Medium)-F12 culture medium. The plates were washed one time with DMEM-F12 medium. 100 1p of the Fluo-4 containing-DMEM-F12 medium were added to the HEK-cells which were incubated for 1.5-2 h in this fluorescent medium. Fluo-4 is taken up by the cytoplasm of the cells.

Buffer: 145 mM NaCl, 5 mM KCl, 1 mM MgCl2, 10 mM Hepes, 10 mM Glucose, EGTA (Ethylene-bis oxyethylene nitrilo tetraacetic acid). The pH was adjusted to 7.4.

Performance of the assay: A minimum of 80 μl/well of compound (3Z,5S)-5-(hydroxymethyl)-1-[(2'-methyl-1,1'-biphenyl-4-yl)carbonyl]pyrrolidin-3-one O-methyloxime (5×) in the above buffer (1×) were prepared (96-well-plates). The compound (3Z,5S)-5-(hydroxymethyl)-1-[(2'-methyl-1,1'-biphenyl-4-yl)carbonyl]pyrrolidin-3-one O-methyloxime was added to the 96-well-plates at different concentrations (30 μM, 10 μM, 1 μM, 300 nM, 100 nM, 10 nM, 1 nM, 100 pM, 10 pM). Oxytocin (OT) was added at a concentration of 40 nM.

The relative fluorescence of Fluo-4 (λex=488 nm, λem=590 nm) is then measured by the FLIPR in presence or absence of compounds (3Z,5S)-5-(hydroxymethyl)-1-[(2'-methyl-1,1'-biphenyl-4-yl)carbonyl]pyrrolidin-3-one O-methyloxime. The fluorescence of the marker being sensitive to the amount of Ca2+, the Ca2+ movements can be detected. Then, it can be determined the ability of compound (3Z,5S)-5-(hydroxymethyl)-1-[(2'-methyl-1,1'-biphenyl-4-yl)carbonyl]pyrrolidin-3-one O-methyloxime to antagonize the oxytocin-induced intracellular Ca2+ mobilization mediated by the oxytocin receptor.

The compound of formula (3Z,5S)-5-(hydroxymethyl)-1-[(2'-methyl-1,1'-biphenyl-4-yl)carbonyl]pyrrolidin-3-one O-methyloxime inhibits the activity of oxytocin on OT-R with an IC50=81 nM.

Example 4: Inhibition of Spontaneous Uterine Contractions in Anesthetized Late-Term Pregnant Rat 4.1 Experimental Protocol Late-term pregnant (certified at days 19-21 of pregnancy) Sprague Dawley CD (SD) BR female rats (Charles River, Calco, Italy), weighing 350-400 g were anesthetized with urethane (1.05 g/kg, i.p.) and placed on a homeothermic operating table. A midline incision at the hypogastrium level was made, one pregnant uterine horn exposed and its tubal end (near the ovary) was closed by a ligature with surgical silk.

Corresponding to the fetus close to the ovary, the uterine-horn wall was incised taking care not to injure the adjacent placenta and PE240 tubing with a latex balloon (9 mm length when empty, capacity 0.1 mL; Radnoti, Monrovia, Calif., USA) on the top was inserted into the lumen and secured to the uterine wall with surgical silk. After filling the internal cavity of the latex balloon with 0.1 mL of sterile physiological saline solution, the catheter was connected to an amplifying/recording system (MacLab. ADInstruments Pty Ltd, Castle Hill, Australia) via a P23ID Gould-Statham pressure transducer. One jugular vein was isolated and cannulated with a PE60 polyethylene cannula for the i.v. administration. After the surgical preparation, a 30-min stabilization period was observed and then the effects of increasing doses of compounds of the present invention (given as 10-min i.v. infusion, bolus i.v. or p.o.) were evaluated by measuring the resulting uterine contractions.

For the i.v. administration (infusion or bolus) the uterine contractile activity was quantified by calculating the AUC during the 10-min injection period. The percent variation of the AUC values relative to the spontaneous uterine response observed after each compound administration was calculated in comparison to the value recorded before the first dose-administration (basal value). The effect of test compounds of the present invention was evaluated by comparing pre- and post-treatment luminal uterine pressure values.

For the oral administration the same computation procedure was applied at different time points after treatment. Statistical differences between treatment groups at each time-point were determined by using one-way ANOVA followed by Tukey test.

4.2 Results

FIGS. 1A and B describe dose-response effects of Z-isomer and E-isomer administered by oral route on inhibition of spontaneous uterine contractions in anesthetized pregnant rats near term (gestational days 19-21). Data as means±S.E. of n=6-8 animals per group. The y-axis represents uterine contractions as % of value compared to pre-dose set at 100%. The x-axis represents the time post-dose in minutes. Contractions were continuously recorded and area-under-the-curve (AUC) integrated over 10-min time intervals.

The results presented on FIG. 1A demonstrate that (3Z,5S)-5-(hydroxymethyl)-1-[(2'-methyl-1,1'-biphenyl-4-yl)carbonyl]pyrrolidin-3-one O-methyloxime (Z form) is capable to rapidly inhibit spontaneous uterine contractions in anesthetized late-term pregnant rat at various doses (10, 30 or 60 mg/kg) compared to control vehicle NP3S (5% N-methylpyrrolidone, 25% polyethyleneglycol 200, 30% polyethylene glycol 400, 20% propylene glycol, 20% saline). Uterine contractions inhibition of 15% can be observed 5 to 15 min after administration of the substantially pure Z form. Efficient inhibition of 42% is observed 170-180 minutes after administration of said compound.

In contrast, no inhibition of uterine contraction has been observed with (3E,5S)-5-(hydroxymethyl)-1-[(2'-methyl-1,1'-biphenyl-4-yl)carbonyl]pyrrolidin-3-one O-methyloxime at various doses (10, 30 or 60 mg/kg, E form) at any time during the 170-180 minutes observation (FIG. 1B).

Surprisingly, the present invention shows that the substantially pure Z form having formula (3Z,5 S)-5-(hydroxymethyl)-1-[(2'-methyl-1,1'-biphenyl-4-yl)carbonyl]pyrrolidin-3-one O-methyloxime inhibits uterine contraction whereas the substantially pure E form has no efficacy. Thus, the present invention advantageously relates to biologically active compounds of formula (3Z,5S)-5-(hydroxymethyl)-1-[(2'-methyl-1,1'-biphenyl-4-yl)carbonyl]pyrrolidin-3-one O-methyloxime and/or metabolite thereof in substantially pure form that can be administered at lower dosage compared to said compounds provided in isomeric mixture.

Example 5: In Vivo Stability of (3Z,5S)-5-(hydroxymethyl)-1-[(2'-methyl-1,1'-biphenyl-4-yl)carbonyl]pyrrolidin-3-one O-methyloxime The isomeric interconversion of [$^{14}$C]- (3Z,5S)-5-(hydroxymethyl)-1-[(2'-methyl-1,1'-biphenyl-4-yl)carbonyl]pyrrolidin-3-one O-methyloxime was studied after single oral and intravenous doses (nominal 30 mg/kg, 25 µCi/rat) to eight healthy female rats (n=4 for each dose route).

The animals used in this study were Sprague-Dawley, Crl:CD®BR albino rats. All animals were supplied by Charles River UK Ltd (Margate, Kent, UK). Animals were in the weight range 200-260 g and were approximately 2 months old. Rats were given a unique identity number and were identified by unique tail markings plus cage location.

The dose groups were as follows: 4 female were given an oral dose and 4 female were given an intravenous dose.

[$^{14}$C]- (3Z,5S)-5-(hydroxymethyl)-1-[(2'-methyl-1,1'-biphenyl-4-yl)carbonyl]pyrrolidin-3-one O-methyloxime oral and intravenous dosing formulations were prepared separately at each dose phase at a target dose level of 30 mg/kg, and at a radioactive concentration of approximately 25 µCi/rat. Dose formulations were prepared in an appropriate matrix; intravenous doses were prepared in NP3S, whilst oral doses were prepared in Labrasol:water (1:1 v/v).

Chromatographic analysis using HPLC indicated that radioactive components exhibiting co-chromatography with the E-isomer of formula (3E,5S)-5-(hydroxymethyl)-1-[(2'-methyl-1,1'-biphenyl-4-yl)carbonyl]pyrrolidin-3-one O-methyloxime were not present in the oral or intravenous dose formulations either pre- or post-dose administration. There was therefore no detectable interconversion of (3Z,5S)-5-(hydroxymethyl)-1-[(2'-methyl-1,1'-biphenyl-4-yl)carbonyl]pyrrolidin-3-one O-methyloxime to (3E,5S)-5-(hydroxymethyl)-1-[(2'-methyl-1,1'-biphenyl-4-yl)carbonyl]pyrrolidin-3-one O-methyloxime during dose preparation or administration. There was no evidence that [$^{14}$C]- E-isomer of formula (3E,5S)-5-(hydroxymethyl)-1-[(2'-methyl-1,1'-biphenyl-4-yl)carbonyl]pyrrolidin-3-one O-methyloxime was present in plasma collected up to 6 hours after an oral or intravenous administration of [$^{14}$C]-(3Z,5S)-5-(hydroxymethyl)-1-[(2'-methyl-1,1'-biphenyl-4-yl)carbonyl]pyrrolidin-3-one O-methyloxime.

Therefore, using the methods described [$^{14}$C]- (3Z,5S)-5-(hydroxymethyl)-1-[(2'-methyl-1,1'-biphenyl-4-yl)carbonyl]pyrrolidin-3-one O-methyloxime undergoes no detectable isomeric interconversion in vivo after oral or intravenous dose administration.

The invention claimed is:

1. A method of synthesizing a compound, (3Z,5S)-5-(hydroxymethyl)-1-[(2'-methyl-1,1'-biphenyl-4-yl)carbonyl]pyrrolidin-3-one O-methyloxime, represented by formula (I)

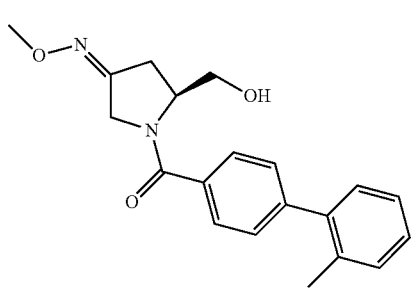
(I)

said method comprising reducing a precursor, methyl (2S,4Z)-1-[(2'-methyl-1,1'-biphenyl-4-yl)carbonyl]-4-methoxyimino pyrrolidine-2-carboxylate, represented by formula (II)

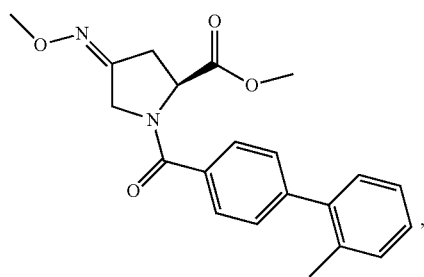
(II)

thereby producing said compound represented by formula (I).

2. The method of claim 1, wherein said precursor represented by formula (II) is present within a mixture comprising a diastereomer, methyl (2S,4E)-1-[(2'-methyl-1,1'-biphenyl-4-yl)carbonyl]-4-methoxyimino pyrrolidine-2-carboxylate, represented by formula (IIa)

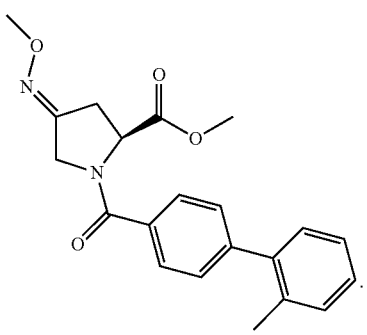
(IIa)

3. The method of claim 1, wherein said reducing comprises reacting said precursor represented by formula (II) with lithium borohydride.

4. The method of claim 3, said method comprising reacting said precursor represented by formula (II) with said lithium borohydride in a solvent comprising methanol and tetrahydrofuran.

5. The method of claim 1, said method comprising synthesizing said precursor represented by formula (II) by O-methylating a precursor represented by formula (III)

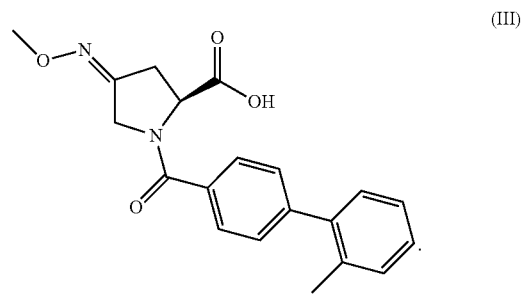 [SMILES: CO/N=C1/C[C@@H](C(=O)OC)N(C(=O)c2ccc(-c3ccccc3C)cc2)C1]
(III)

6. The method of claim 5, wherein said O-methylating comprises reacting said precursor represented by formula (III) with dimethyl sulfate.

7. The method of claim 6, said method comprising reacting said precursor represented by formula (III) with said dimethyl sulfate in the presence of a base.

8. The method of claim 7, wherein said base is potassium carbonate.

9. The method of claim 5, said method comprising synthesizing said precursor represented by formula (III) by reacting a precursor represented by formula (IV)

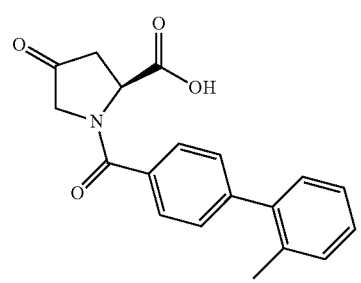
(IV)

with methoxyamine or a salt thereof.

10. The method of claim 9, said method comprising reacting said precursor represented by formula (IV) with methoxyamine hydrochloride.

11. The method of claim 9, said method comprising synthesizing said precursor represented by formula (IV) by oxidizing a precursor represented by formula (V)

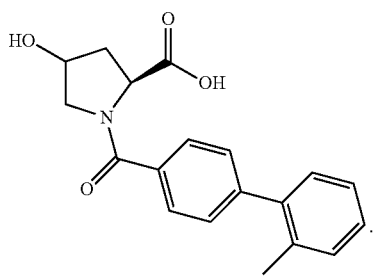
(V)

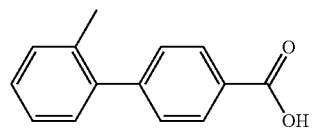
(VIII)

with thionyl chloride.

17. The method of claim 16, said method comprising synthesizing said precursor represented by formula (VIII) by coupling a precursor represented by formula (IX)

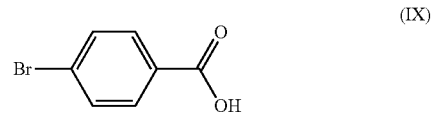
(IX)

12. The method of claim 11, wherein said oxidizing comprises reacting said precursor represented by formula (V) with pyridine-sulfur trioxide.

13. The method of claim 11, wherein said precursor represented by formula (V) is a precursor represented by formula (Va)

with a precursor represented by formula (X)

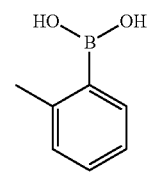
(X)

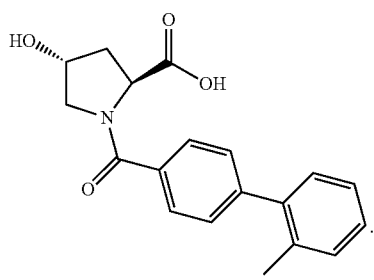
(Va)

under Suzuki reaction conditions.

18. The method of claim 17, wherein said coupling comprises reacting said precursor represented by formula (IX) with said precursor represented by formula (X) in the presence of tetrakis(triphenylphosphine)palladium.

19. A method of treating a human patient undergoing embryo transfer, said method comprising administering to said patient a therapeutically effective amount of a compound, (3Z,5S)-5-(hydroxymethyl)-1-[(2'-methyl-1,1'-biphenyl-4-yl)carbonyl]pyrrolidin-3-one O-methyloxime, represented by formula (I)

14. The method of claim 13, said method comprising synthesizing said precursor represented by formula (Va) by reacting a precursor represented by formula (VI)

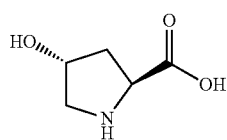
(VI)

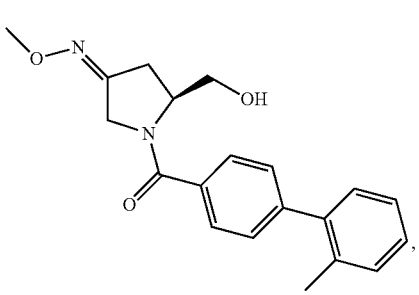
(I)

with a precursor represented by formula (VII)

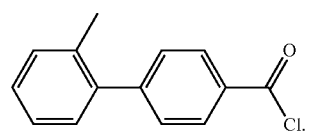
(VII)

15. The method of claim 14, said method comprising reacting said precursor represented by formula (VI) with said precursor represented by formula (VII) and potassium carbonate.

16. The method of claim 14, said method comprising synthesizing said precursor represented by formula (VII) by reacting a precursor represented by formula (VIII)

thereby reducing the likelihood of embryo implantation failure in said patient.

20. The method of claim 19, wherein said embryo transfer comprises in vitro fertilization thereby producing one or more embryos, followed by transfer of said one or more embryos to said patient.

21. The method of claim 19, said method comprising administering said compound represented by formula (I) to said patient orally, intravenously, or vaginally.

22. The method of claim 19, said method comprising administering said compound represented by formula (I) to said patient in combination with one or more pharmaceutically acceptable carriers, diluents, or excipients.

23. The method of claim 19, wherein said compound has a purity that is at least in the range of from 85% to 99.9% with respect to a diastereomer of the formula (3E,5S)-5-(hydroxymethyl)-1-[(2'-methyl-1,1'-biphenyl-4-yl)carbonyl]pyrrolidin-3-one O-methyloxime.

24. The method of claim 23, wherein said compound has a purity of at least 90% with respect to a diastereomer of the formula (3E,5S)-5-(hydroxymethyl)-1-[(2'-methyl-1, 1'-biphenyl-4-yl)carbonyl]pyrrolidin-3-one O-methyloxime.

25. The method of claim 24, wherein said compound has a purity of at least 95% with respect to a diastereomer of the formula (3E,5S)-5-(hydroxymethyl)-1-[(2'-methyl-1,1'-biphenyl-4-yl)carbonyl]pyrrolidin-3-one O-methyloxime.

26. The method of claim 25, wherein said compound has a purity of from about 95% to about 99.9% with respect to a diastereomer of the formula (3E,5S)-5-(hydroxymethyl)-1-[(2'-methyl-1,1'-biphenyl-4-yl)carbonyl]pyrrolidin-3-one O-methyloxime.

* * * * *

UNITED STATES PATENT AND TRADEMARK OFFICE
CERTIFICATE OF CORRECTION

| | | |
|---|---|---|
| PATENT NO. | : 10,047,048 B2 | Page 1 of 2 |
| APPLICATION NO. | : 15/476325 | |
| DATED | : August 14, 2018 | |
| INVENTOR(S) | : Andre Chollet | |

It is certified that error appears in the above-identified patent and that said Letters Patent is hereby corrected as shown below:

On the Title Page

Under OTHER PUBLICATIONS, in Pierzynski, replace "Oxytocin...Assisted Reproduction, vol. 22" with --"Oxytocin...Assisted Reproduction," Reproductive biomedicine online, vol. 22--.

Under OTHER PUBLICATIONS, in Visnova, replace "Effects...Stimulation, pp.242 (2012)" with --"P-242. Effects...Stimulation," S183 (2012).--.

Page 2, under OTHER PUBLICATIONS, in Vrachnis et al, replace "Jan. 8, 2011" with --pp. 1-8. (2011)--.

In the Specification

Column 2, Line 40, replace "lighthcadedness" with --lightheadedness--.

Column 3, Line 47, replace "polyethyleneglycol" with --polyethylene glycol--.

Column 7, Line 20, replace "i.e" with --i.e.--.

Column 14, Line 14, replace "val" with --vol--;
    Line 56, replace "C.3" with --C.--.

Column 16, Line 43, replace "hours). 7" with --hours).--.

Column 19, Line 53, replace "val" with --vol--.

Column 20, Line 8, replace "(31/E,5S)" with --(3Z/E,5S)--.

Signed and Sealed this
Twenty-second Day of December, 2020

Andrei Iancu
*Director of the United States Patent and Trademark Office*

CERTIFICATE OF CORRECTION (continued)
U.S. Pat. No. 10,047,048 B2

Column 26, Line 38, replace "Dubecco's" with --Dulbecco's--.

Column 27, Line 66, replace "polyethyleneglycol" with --polyethylene glycol--.